(12) United States Patent
Harbeson

(10) Patent No.: US 10,357,499 B2
(45) Date of Patent: Jul. 23, 2019

(54) SUBSTITUTED TRIAZOLOBENZODIAZEPINES

(71) Applicant: Concert Pharmaceuticals, Inc., Lexington, MA (US)

(72) Inventor: Scott L. Harbeson, Cambridge, MA (US)

(73) Assignee: Concert Pharmaceutical, Inc., Lexington, MA (US)

( * ) Notice: Subject to any disclaimer, the term of this patent is extended or adjusted under 35 U.S.C. 154(b) by 0 days.

(21) Appl. No.: 16/025,512

(22) Filed: Jul. 2, 2018

(65) Prior Publication Data

US 2018/0303848 A1  Oct. 25, 2018

Related U.S. Application Data

(63) Continuation of application No. 15/610,153, filed on May 31, 2017, now Pat. No. 10,039,769, which is a continuation of application No. 15/117,544, filed as application No. PCT/US2015/015034 on Feb. 9, 2015, now Pat. No. 9,694,017.

(60) Provisional application No. 61/937,701, filed on Feb. 10, 2014.

(51) Int. Cl.
| | |
|---|---|
| *A61K 31/551* | (2006.01) |
| *A61K 31/5517* | (2006.01) |
| *A61K 45/06* | (2006.01) |
| *C07D 487/04* | (2006.01) |
| *C07B 59/00* | (2006.01) |

(52) U.S. Cl.
CPC .......... *A61K 31/5517* (2013.01); *A61K 45/06* (2013.01); *C07B 59/002* (2013.01); *C07D 487/04* (2013.01); *C07B 2200/05* (2013.01); *Y02A 50/411* (2018.01)

(58) Field of Classification Search
CPC .. A61K 31/551; A61K 31/5517; A61K 45/06; C07D 487/04; C07B 59/00
See application file for complete search history.

(56) References Cited

U.S. PATENT DOCUMENTS

| | | | |
|---|---|---|---|
| 6,221,335 B1 | 4/2001 | Foster | |
| 6,440,710 B1 | 8/2002 | Keinan et al. | |
| 6,603,008 B1 | 8/2003 | Ando et al. | |
| 7,517,990 B2 | 4/2009 | Ito et al. | |
| 9,694,017 B2 | 7/2017 | Harbeson | |
| 10,039,769 B2 | 8/2018 | Harbeson | |
| 2005/0176814 A1 | 8/2005 | Alken | |
| 2007/0082929 A1 | 4/2007 | Gant et al. | |
| 2007/0197695 A1 | 8/2007 | Potyen et al. | |
| 2008/0103122 A1 | 5/2008 | Veltri | |
| 2012/0220573 A1 | 8/2012 | Gosmini et al. | |
| 2012/0252781 A1 | 10/2012 | Bailey et al. | |
| 2014/0213575 A1 | 7/2014 | Schmees | |
| 2016/0346296 A1 | 12/2016 | Harbeson | |
| 2017/0258807 A1 | 9/2017 | Harbeson | |
| 2018/0303848 A1 | 10/2018 | Harbeson | |

FOREIGN PATENT DOCUMENTS

| | | |
|---|---|---|
| JP | AH 09-510717 | 10/1997 |
| JP | A 2005-511742 | 4/2005 |
| WO | WO 1995/26325 | 10/1995 |
| WO | WO 2007/118651 | 10/2007 |
| WO | WO 2011/054553 | 5/2011 |
| WO | WO 2011/143669 | 11/2011 |
| WO | WO 2012/143413 | 10/2012 |
| WO | WO 2013/030150 | 3/2013 |

OTHER PUBLICATIONS

Baillie, "The Use of Stable Isotopes in Pharmacological Research," *Pharmacology Rev*, 1981, 33(2):81-132.
Blake et al., "Studies with Deuterated Drugs", J. Pharm. Sci. v.64, pp. 367-391, 1975.
Browne, "Stable Isotope Techniques in Early Drug Development: An Economic Evaluation," J. Clin. Pharmacology, 1998, 38: 213-20.
Buteau, K., "Deuterated drugs: Unexpectedly Nonobvious?", J. High Technology Law, v. X, No. 1, pp. 22-74, 2009.
Cherrah et al., "Study of Deuterium Isotope Effects on Protein Binding by Gas Chromatography/Mass Spectrometry. Caffeine and Deuterated Isotopomers," Biomed. and Environmental Mass Spectrometry, 1987, 14: 653-57.
Dyck et al., "Effects of Deuterium Substitution on the Catabolism of β-Phenylethylamine: An In Vivo Study," J. Neurochemistry, 1986, 46: 399-404.
Fisher et al., "The complexities inherent in attempts to decrease drug clearance by blocking sites of CYP-mediated metabolism," Curr. Opin. Drug Discov. Dev., 2006, 9(1):101-109.

(Continued)

*Primary Examiner* — Brenda L Coleman
(74) *Attorney, Agent, or Firm* — Fish & Richardson P.C.

(57) ABSTRACT

This invention relates to novel substituted triazolobenzodiazepines of the Formula I:

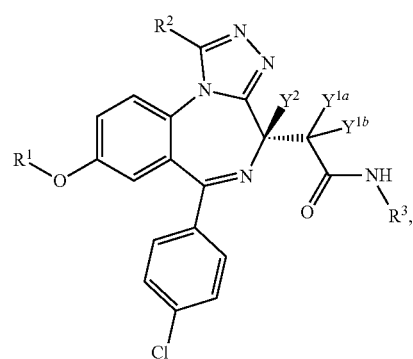

wherein each of the variables are defined herein and pharmaceutically acceptable salts thereof. This invention also provides compositions comprising a compound of this invention and the use of such compositions in methods of treating diseases and conditions that are beneficially treated by administering I-BET762.

14 Claims, No Drawings

(56) References Cited

OTHER PUBLICATIONS

Foster, "Deuterium isotope effects in studies of drug metabolism," Trends in Pharmaceutical Sciences, 1984, 524-527.

Foster, "Deuterium Isotope Effects in the Metabolism of Drugs and Xenobiotics: Implications for Drug Design," Adv. Drug Res., 1985, 14: 2-40.

Fukuto et al. "Determination of the mechanism of demethylenation of (methylenedioxy) phenyl compounds by cytochrome P450 using deuterium isotope effects." Journal of medicinal chemistry, Sep. 1991, 34:2871-2876.

Gouyette, "Synthesis of Deuterium-labelled Elliptinium and its Use in Metabolic Studies," Biomed. and Environmental Mass Spectrometry, 1988, 15: 243-47.

Haskins, "The Application of Stable Isotopes in Biomedical Research," Biomed. Spectrometry, 1982, 9(7):269-77.

Houma et al., "The Metabolism of Roxatidine Acetate Hydrochloride," Drug Metab. Dispos, 1987, 15(4): 551-559.

International Preliminary Report on Patentability in International Application No. PCT/US2015/015034, dated Aug. 25, 2016, 6 pages.

International Search Report and Written Opinion in International Application No. PCT/US2015/015034, dated Apr. 2, 2015, 8 pages.

Kushner et al. "Pharmacological uses and perspectives of heavy water and deuterated compounds," Can. J. Physiol. Pharmacol. 1999, 77: 79-88.

Pieniaszek et al., "Moricizine bioavailability via simultaneous, dual, stable isotope administrations: bioequivalence," J. Clin. Pharmacology, 1999, 39:817-25.

Sanderson, "Big interest in heavy drugs", Nature, v.458, pp. 269, 2009.

Tonn et al., "Simultaneous Analysis of Diphenhydramine and a Stable Isotope Analog ($^2$H10) Diphenhydramine Using Capillary Gas Chromatography with Mass Selective Detection in Biological Fluids from Chronically Instrumented Pregnant Ewes," Biol. Mass Spectrometry, 1993, 22:633-642.

Wolen, "The Application of Stable Isotopes to Studies of Drug Bioavailability and Bioequivalence," J. Clin. Pharmacology, 1986, 26:419-424.

SUBSTITUTED TRIAZOLOBENZODIAZEPINES

CROSS-REFERENCE TO RELATED APPLICATIONS

This application is a continuation application of U.S. application Ser. No. 15/610,153, filed May 31, 2017 know U.S. Pat. No. 10,039,769), which is a continuation of U.S. application Ser. No. 15/117,544, filed Aug. 9, 2016 (now U.S. Pat. No. 9,694,017), which is a National Stage application under 35 U.S.C. § 371 of International Application No. PCT/US2015/015034, filed Feb. 9, 2015, which claims the benefit of U.S. Provisional Application Ser. No. 61/937,701, filed Feb. 10, 2014. The disclosures of the prior applications are considered part of and are incorporated by reference in the disclosure of this application.

BACKGROUND OF THE INVENTION

Many current medicines suffer from poor absorption, distribution, metabolism and/or excretion (ADME) properties that prevent their wider use or limit their use in certain indications. Poor ADME properties are also a major reason for the failure of drug candidates in clinical trials. While formulation technologies and prodrug strategies can be employed in some cases to improve certain ADME properties, these approaches often fail to address the underlying ADME problems that exist for many drugs and drug candidates. One such problem is rapid metabolism that causes a number of drugs, which otherwise would be highly effective in treating a disease, to be cleared too rapidly from the body. A possible solution to rapid drug clearance is frequent or high dosing to attain a sufficiently high plasma level of drug. This, however, introduces a number of potential treatment problems such as poor patient compliance with the dosing regimen, side effects that become more acute with higher doses, and increased cost of treatment. A rapidly metabolized drug may also expose patients to undesirable toxic or reactive metabolites.

Another ADME limitation that affects many medicines is the formation of toxic or biologically reactive metabolites. As a result, some patients receiving the drug may experience toxicities, or the safe dosing of such drugs may be limited such that patients receive a suboptimal amount of the active agent. In certain cases, modifying dosing intervals or formulation approaches can help to reduce clinical adverse effects, but often the formation of such undesirable metabolites is intrinsic to the metabolism of the compound.

In some select cases, a metabolic inhibitor will be co-administered with a drug that is cleared too rapidly. Such is the case with the protease inhibitor class of drugs that are used to treat HIV infection. The FDA recommends that these drugs be co-dosed with ritonavir, an inhibitor of cytochrome P450 enzyme 3A4 (CYP3A4), the enzyme typically responsible for their metabolism (see Kempf, D. J. et al., Antimicrobial agents and chemotherapy, 1997, 41(3): 654-60). Ritonavir, however, causes adverse effects and adds to the pill burden for HIV patients who must already take a combination of different drugs. Similarly, the CYP2D6 inhibitor quinidine has been added to dextromethorphan for the purpose of reducing rapid CYP2D6 metabolism of dextromethorphan in a treatment of pseudobulbar affect. Quinidine, however, has unwanted side effects that greatly limit its use in potential combination therapy (see Wang, L et al., Clinical Pharmacology and Therapeutics, 1994, 56(6 Pt 1): 659-67; and FDA label for quinidine at www.accessdata.fda.gov).

In general, combining drugs with cytochrome P450 inhibitors is not a satisfactory strategy for decreasing drug clearance. The inhibition of a CYP enzyme's activity can affect the metabolism and clearance of other drugs metabolized by that same enzyme. CYP inhibition can cause other drugs to accumulate in the body to toxic levels.

A potentially attractive strategy for improving a drug's metabolic properties is deuterium modification. In this approach, one attempts to slow the CYP-mediated metabolism of a drug or to reduce the formation of undesirable metabolites by replacing one or more hydrogen atoms with deuterium atoms. Deuterium is a safe, stable, non-radioactive isotope of hydrogen. Compared to hydrogen, deuterium forms stronger bonds with carbon. In select cases, the increased bond strength imparted by deuterium can positively impact the ADME properties of a drug, creating the potential for improved drug efficacy, safety, and/or tolerability. At the same time, because the size and shape of deuterium are essentially identical to those of hydrogen, replacement of hydrogen by deuterium would not be expected to affect the biochemical potency and selectivity of the drug as compared to the original chemical entity that contains only hydrogen.

The effects of deuterium substitution on drug metabolism are variable and unpredictable. See, for example, Fisher, M B et al, Curr Opin Drug Discov Devel, 2006, 9:101-09 ("Fisher"). For some compounds deuteration causes decreased metabolic clearance in vivo. For others, there is no change in metabolism. Still others demonstrate increased metabolic clearance. The variability in deuterium effects has led experts to question or dismiss deuterium modification as a viable drug design strategy for inhibiting adverse metabolism (see Foster at p. 35 and Fisher at p. 101).

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its non-deuterated counterpart. See, for example, Fukuto et al. (J. Med. Chem. 1991, 34, 2871-76). Many drugs have multiple sites where metabolism is possible. The site(s) where deuterium substitution is required and the extent of deuteration necessary to see an effect on metabolism, if any, will be different for each drug.

I-BET762, also known as 2-[6-(4-chlorophenyl)-8-methoxy-1-methyl-4H-[1,2,4]triazolo[4,3-a][1,4]benzodiazepin-4(S)-yl]-N-ethylacetamide, is known to inhibit bromodomain-containing proteins 2 (Brd2), 3 (Brd3) and 4 (Brd4) that induce the expression and production of apolipoprotein A-1 (ApoA-1) in human hepatocyte Hep G2 cells. Bromodomains are protein domains that bind and recognize histone acetylation. Six families of bromodomain containing proteins are known. These bromodomain-containing proteins monitor histone acetylation and regulate epigenically controlled processes such as chromatin remodeling and gene transcription. The BET family includes the proteins—Brd2, Brd3 and Brd4 which are potential cancer targets. Compounds such as I-BET762 can be used for the treatment of neoplasia, acute and chronic inflammatory disease, autoimmune disorders, obesity, fatty liver, diabetes, atherosclerosis, arterial stent occlusion, heart failure, cachexia, graft versus host disease, infectious diseases associated with bromodomains, treatment of parasites, malaria, trypanosomes and for reducing male fertility. I-BET762 is currently undergoing clinical evaluation for NUT midline carcinoma or NMC (NUT refers to the nuclear protein in testis) and for hematologic cancer.

Despite the beneficial activities of I-BET762, there is a continuing need for new compounds to treat the aforementioned diseases and conditions.

SUMMARY OF THE INVENTION

This invention relates to novel substituted triazolobenzodiazepines, and pharmaceutically acceptable salts thereof. This invention also provides compositions comprising a compound of this invention and the use of such compositions in methods of treating diseases and conditions that are beneficially treated by administering inhibitors of bromodomains, particularly inhibitors of BET bromodomains.

DETAILED DESCRIPTION OF THE INVENTION

Definitions

The term "treat" means decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

It will be recognized that in a synthesized compound, the small amounts of deuterium that will vary depending upon the origin of chemical materials used in the synthesis. Thus, preparations of I-BET762 will inherently contain deuterated isotopologues in various small amounts. Notwithstanding this variation, the abundance of deuterium in I-BET762 is small and immaterial as compared to the degree of deuterium substitution in compounds of this invention. See, for instance, Wada, E et al., Seikagaku, 1994, 66:15; Gannes, L Z et al., Comp Biochem Physiol Mol Integr Physiol, 1998, 119:725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species in which the chemical structure differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

The invention also provides salts of the compounds of the invention.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The compounds of the present invention (e.g., compounds of Formula I), may contain an asymmetric carbon atom, for example, as the result of deuterium substitution or otherwise. As such, compounds of this invention can exist as either individual enantiomers, or mixtures of the two enantiomers. Accordingly, a compound of the present invention may exist as either a racemic mixture or a scalemic mixture, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. "Stereoisomer" refers to both enantiomers and diastereomers. "Tert" and "t-" each refer to tertiary. "US" refers to the United States of America.

"Substituted with deuterium" refers to the replacement of one or more hydrogen atoms with a corresponding number of deuterium atoms.

Throughout this specification, a variable may be referred to generally (e.g., "each $Y^1$") or may be referred to specifically (e.g., $Y^{1a}$ or $Y^{1b}$). Unless otherwise indicated, when a variable is referred to generally, it is meant to include all specific embodiments of that particular variable.

Therapeutic Compounds

The present invention provides a compound of Formula I:

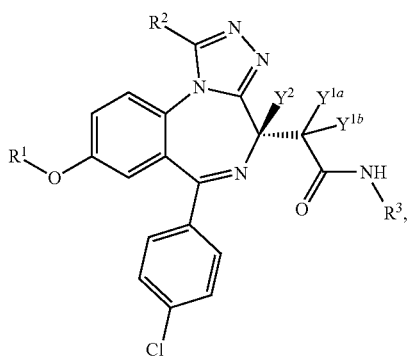

(I)

or a pharmaceutically acceptable salt, wherein $Y^{1a}$, $Y^{1b}$ and $Y^2$ are each independently selected from hydrogen and deuterium;

$R^1$ and $R^2$ are each methyl and are independently substituted with 0 to 3 deuterium;

$R^3$ is ethyl and is substituted with 0 to 5 deuterium; and if $R^1$ and $R^2$ are each $CH_3$, $R^3$ is $CH_2CH_3$, and $Y^2$ is hydrogen, then at least one of $Y^{1a}$ and $Y^{1b}$ is deuterium.

In one embodiment of this invention, each $Y^1$ is the same, such that $Y^{1a}$ and $Y^{1b}$ are each hydrogen or $Y^{1a}$ and $Y^{1b}$ are each deuterium. When each $Y^1$ is hydrogen, in one aspect $Y^2$ is deuterium and in another aspect, $Y^2$ is hydrogen. When each $Y^1$ is deuterium, in one aspect $Y^2$ is deuterium and in another aspect $Y^2$ is hydrogen.

In one embodiment of this invention, $R^1$ and $R^2$ are each selected from $CH_3$ and $CD_3$. In aspects of this embodiment, $R^1$ and $R^2$ are each $CH_3$, $R^1$ and $R^2$ are each $CD_3$, $R^1$ is $CD_3$ and $R^2$ is $CH_3$, and $R^1$ is $CH_3$ and $R^2$ is $CD_3$. In further aspects $Y^{1a}$ and $Y^{1b}$ are each hydrogen and in other further aspects $Y^{1a}$ and $Y^{1b}$ are each deuterium.

In one embodiment of this invention, $R^3$ is selected from —$CH_2CH_3$, —$CD_2CH_3$, —$CH_2CD_3$ and —$CD_2CD_3$. In aspects of this embodiment, $R^3$ is —$CH_2CH_3$, $R^3$ is —$CD_2CD_3$, and $R^3$ is —$CD_2CH_3$. Table 1 illustrates various embodiments of this invention wherein each $Y^1$ is the same, $Y^2$ is hydrogen or deuterium, $R^1$ and $R^2$ are independently selected from $CH_3$ and $CD_3$ and $R^3$ is selected from —$CH_2CH_3$, —$CD_2CH_3$, —$CH_2CD_3$ and —$CD_2CD_3$.

TABLE 1

Exemplary Embodiments of Formula I

| Embodiment | $R^1$ | $R^2$ | $R^3$ |
|---|---|---|---|
| I-a | $CH_3$ | $CH_3$ | —$CH_2CH_3$ |
| I-b | $CD_3$ | $CH_3$ | —$CH_2CH_3$ |
| I-c | $CH_3$ | $CD_3$ | —$CH_2CH_3$ |
| I-d | $CH_3$ | $CH_3$ | —$CD_2CH_3$ |
| I-e | $CH_3$ | $CH_3$ | —$CD_2CH_3$ |
| I-f | $CH_3$ | $CH_3$ | —$CH_2CD_3$ |
| I-g | $CD_3$ | $CD_3$ | —$CH_2CH_3$ |
| I-h | $CD_3$ | $CH_3$ | —$CD_2CH_3$ |
| I-i | $CH_3$ | $CD_3$ | —$CD_2CH_3$ |
| I-j | $CD_3$ | $CH_3$ | —$CD_2CH_3$ |
| I-k | $CH_3$ | $CD_3$ | —$CD_2CH_3$ |
| I-l | $CD_3$ | $CH_3$ | —$CH_2CD_3$ |
| I-m | $CH_3$ | $CD_3$ | —$CH_2CD_3$ |
| I-n | $CD_3$ | $CD_3$ | —$CD_2CD_3$ |
| I-o | $CD_3$ | $CD_3$ | —$CH_2CD_3$ |
| I-p | $CD_3$ | $CD_3$ | —$CD_2CH_3$ |

In one embodiment, the compound is a compound of Formula I wherein $Y^{1a}$=$Y^{1b}$=H and is selected from any one of the compounds set forth in Table 2 (below):

TABLE 2

Exemplary Compounds of Formula I

| Compound | $Y^2$ | $R^1$ | $R^2$ | $R^3$ |
|---|---|---|---|---|
| 101 | H | —$CH_3$ | —$CH_3$ | —$CD_2CD_3$ |
| 102 | H | —$CH_3$ | —$CH_3$ | —$CD_2CH_3$ |
| 103 | H | —$CH_3$ | —$CH_3$ | —$CH_2CD_3$ |
| 104 | H | —$CD_3$ | —$CH_3$ | —$CH_2CH_3$ |
| 105 | H | —$CH_3$ | —$CD_3$ | —$CH_2CH_3$ |
| 106 | D | —$CH_3$ | —$CH_3$ | —$CH_2CH_3$ |
| 107 | D | —$CD_3$ | —$CH_3$ | —$CH_2CH_3$ |
| 108 | D | —$CH_3$ | —$CD_3$ | —$CH_2CH_3$ |
| 109 | D | —$CH_3$ | —$CH_3$ | —$CD_2CD_3$ |

TABLE 2-continued

Exemplary Compounds of Formula I

| Compound | $Y^2$ | $R^1$ | $R^2$ | $R^3$ |
|---|---|---|---|---|
| 110 | D | —$CH_3$ | —$CH_3$ | —$CD_2CH_3$ |
| 111 | D | —$CH_3$ | —$CH_3$ | —$CH_2CD_3$ |
| 112 | H | —$CD_3$ | —$CD_3$ | —$CH_2CH_3$ |
| 113 | H | —$CD_3$ | —$CH_3$ | —$CD_2CD_3$ |
| 114 | H | —$CD_3$ | —$CH_3$ | —$CD_2CH_3$ |
| 115 | H | —$CD_3$ | —$CH_3$ | —$CH_2CD_3$ |
| 116 | H | —$CH_3$ | —$CD_3$ | —$CD_2CD_3$ |
| 117 | H | —$CH_3$ | —$CD_3$ | —$CD_2CH_3$ |
| 118 | H | —$CH_3$ | —$CD_3$ | —$CH_2CD_3$ |
| 119 | D | —$CD_3$ | —$CD_3$ | —$CH_2CH_3$ |
| 120 | D | —$CD_3$ | —$CH_3$ | —$CD_2CD_3$ |
| 121 | D | —$CD_3$ | —$CH_3$ | —$CD_2CH_3$ |
| 122 | D | —$CD_3$ | —$CH_3$ | —$CH_2CD_3$ |
| 123 | D | —$CH_3$ | —$CD_3$ | —$CD_2CD_3$ |
| 124 | D | —$CH_3$ | —$CD_3$ | —$CD_2CH_3$ |
| 125 | D | —$CH_3$ | —$CD_3$ | —$CH_2CD_3$ |
| 126 | H | —$CD_3$ | —$CD_3$ | —$CD_2CD_3$ |
| 127 | H | —$CD_3$ | —$CD_3$ | —$CD_2CH_3$ |
| 128 | H | —$CD_3$ | —$CD_3$ | —$CH_2CD_3$ |
| 129 | D | —$CD_3$ | —$CD_3$ | —$CD_2CD_3$ |
| 130 | D | —$CD_3$ | —$CD_3$ | —$CD_2CH_3$ |
| 131 | D | —$CD_3$ | —$CD_3$ | —$CH_2CD_3$ | or a pharmaceutically acceptable salt thereof.

In one embodiment, the compound is a compound of Formula I wherein $Y^{1a}=Y^{1b}=D$ and is selected from any one of the compounds set forth in Table 3 (below):

TABLE 3

Exemplary Compounds of Formula I

| Compound | $Y^2$ | $R^1$ | $R^2$ | $R^3$ |
|---|---|---|---|---|
| 200 | H | —$CH_3$ | —$CH_3$ | —$CH_2CH_3$ |
| 201 | H | —$CH_3$ | —$CH_3$ | —$CD_2CD_3$ |
| 202 | H | —$CH_3$ | —$CH_3$ | —$CD_2CH_3$ |
| 203 | H | —$CH_3$ | —$CH_3$ | —$CH_2CD_3$ |
| 204 | H | —$CD_3$ | —$CH_3$ | —$CH_2CH_3$ |
| 205 | H | —$CH_3$ | —$CD_3$ | —$CH_2CH_3$ |
| 206 | D | —$CH_3$ | —$CH_3$ | —$CH_2CH_3$ |
| 207 | D | —$CD_3$ | —$CH_3$ | —$CH_2CH_3$ |
| 208 | D | —$CH_3$ | —$CD_3$ | —$CH_2CH_3$ |
| 209 | D | —$CH_3$ | —$CH_3$ | —$CD_2CD_3$ |
| 210 | D | —$CH_3$ | —$CH_3$ | —$CD_2CH_3$ |
| 211 | D | —$CH_3$ | —$CH_3$ | —$CH_2CD_3$ |
| 212 | H | —$CD_3$ | —$CD_3$ | —$CH_2CH_3$ |
| 213 | H | —$CD_3$ | —$CH_3$ | —$CD_2CD_3$ |
| 214 | H | —$CD_3$ | —$CH_3$ | —$CD_2CH_3$ |
| 215 | H | —$CD_3$ | —$CH_3$ | —$CH_2CD_3$ |
| 216 | H | —$CH_3$ | —$CD_3$ | —$CD_2CD_3$ |
| 217 | H | —$CH_3$ | —$CD_3$ | —$CD_2CH_3$ |
| 218 | H | —$CH_3$ | —$CD_3$ | —$CH_2CD_3$ |
| 219 | D | —$CD_3$ | —$CD_3$ | —$CH_2CH_3$ |
| 220 | D | —$CD_3$ | —$CH_3$ | —$CD_2CD_3$ |
| 221 | D | —$CD_3$ | —$CH_3$ | —$CD_2CH_3$ |
| 222 | D | —$CD_3$ | —$CH_3$ | —$CH_2CD_3$ |
| 223 | D | —$CH_3$ | —$CD_3$ | —$CD_2CD_3$ |
| 224 | D | —$CH_3$ | —$CD_3$ | —$CD_2CH_3$ |
| 225 | D | —$CH_3$ | —$CD_3$ | —$CH_2CD_3$ |
| 226 | H | —$CD_3$ | —$CD_3$ | —$CD_2CD_3$ |
| 227 | H | —$CD_3$ | —$CD_3$ | —$CD_2CH_3$ |
| 228 | H | —$CD_3$ | —$CD_3$ | —$CH_2CD_3$ |
| 229 | D | —$CD_3$ | —$CD_3$ | —$CD_2CD_3$ |
| 230 | D | —$CD_3$ | —$CD_3$ | —$CD_2CH_3$ |
| 231 | D | —$CD_3$ | —$CD_3$ | —$CH_2CD_3$ | or a pharmaceutically acceptable salt thereof.

In another set of embodiments, any atom not designated as deuterium in any of the embodiments set forth above is present at its natural isotopic abundance.

The synthesis of compounds of Formula I may be readily achieved by synthetic chemists of ordinary skill by reference to the Exemplary Synthesis and Examples disclosed herein. Relevant procedures analogous to those of use for the preparation of compounds of Formula I and intermediates thereof are disclosed, for instance in US2012220573 and US2012252781.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Exemplary Synthesis

A convenient method for synthesizing compounds of Formula I is depicted in Scheme 1, below.

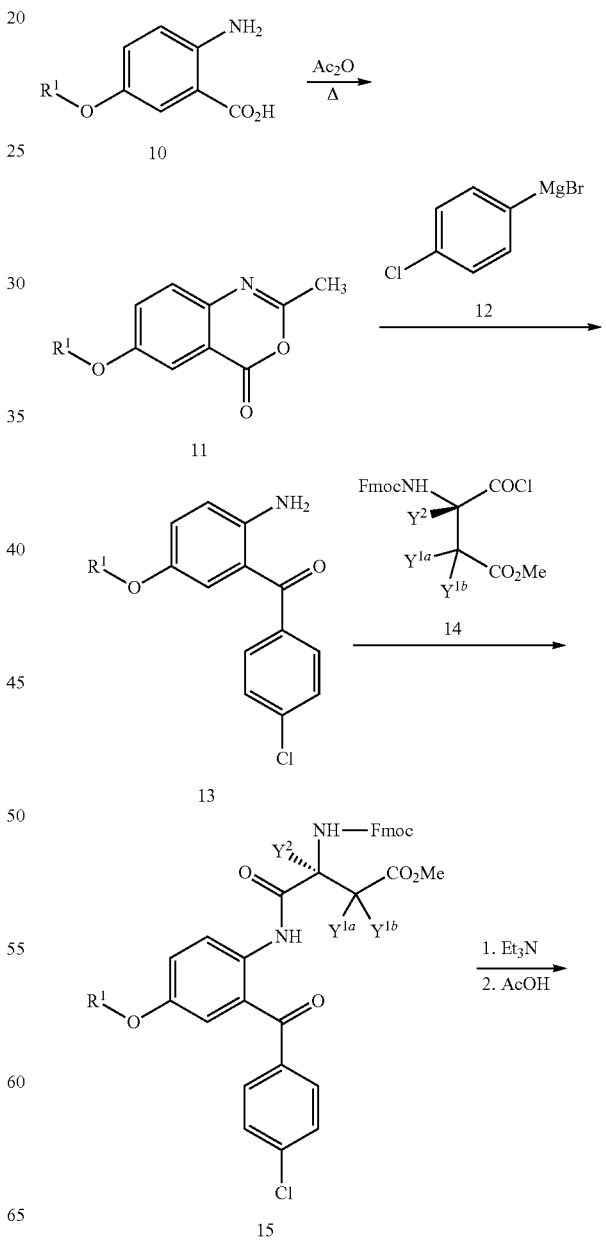

Scheme 1. Synthesis of Compounds of Formula I

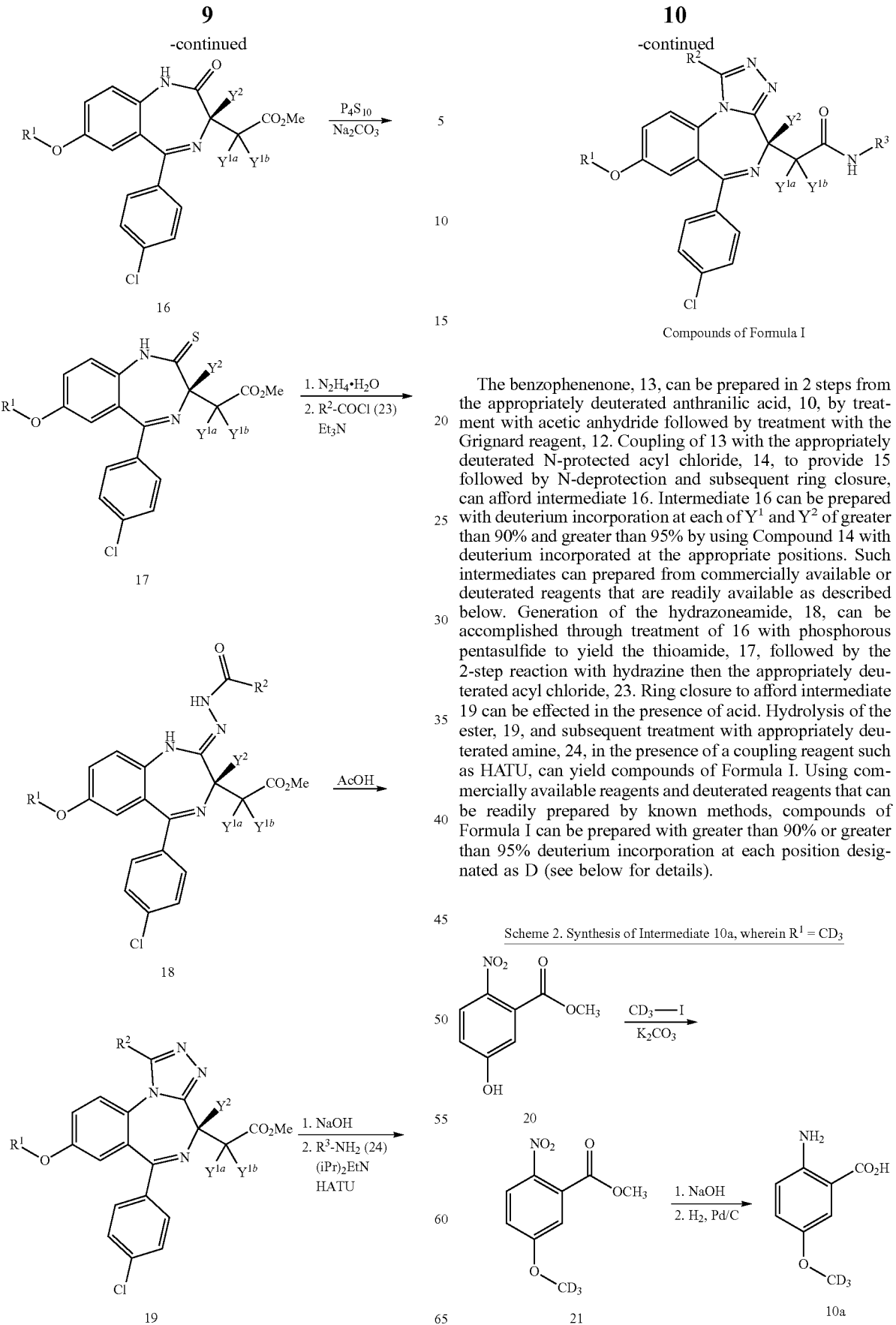

The benzophenenone, 13, can be prepared in 2 steps from the appropriately deuterated anthranilic acid, 10, by treatment with acetic anhydride followed by treatment with the Grignard reagent, 12. Coupling of 13 with the appropriately deuterated N-protected acyl chloride, 14, to provide 15 followed by N-deprotection and subsequent ring closure, can afford intermediate 16. Intermediate 16 can be prepared with deuterium incorporation at each of $Y^1$ and $Y^2$ of greater than 90% and greater than 95% by using Compound 14 with deuterium incorporated at the appropriate positions. Such intermediates can prepared from commercially available or deuterated reagents that are readily available as described below. Generation of the hydrazoneamide, 18, can be accomplished through treatment of 16 with phosphorous pentasulfide to yield the thioamide, 17, followed by the 2-step reaction with hydrazine then the appropriately deuterated acyl chloride, 23. Ring closure to afford intermediate 19 can be effected in the presence of acid. Hydrolysis of the ester, 19, and subsequent treatment with appropriately deuterated amine, 24, in the presence of a coupling reagent such as HATU, can yield compounds of Formula I. Using commercially available reagents and deuterated reagents that can be readily prepared by known methods, compounds of Formula I can be prepared with greater than 90% or greater than 95% deuterium incorporation at each position designated as D (see below for details).

Starting material, 10a, may be prepared as shown in Scheme 2 using commercially available CD$_3$I, with greater than or equal to 95% or greater than or equal to 99% deuterium incorporation at each position in R$^1$ designated as D. For example CD$_3$I, with deuterium at 99% abundance, is commercially available.

Intermediate 10b, wherein R$^1$=CH$_3$, is commercially available.

The following deuterated reagents are commercially available with deuterium at 98-99.5% abundance:

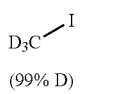

(99% D)

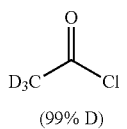

(99% D)

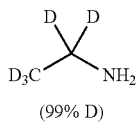

(99% D)

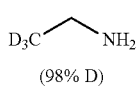

(98% D)

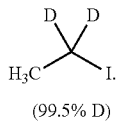

(99.5% D)

The following reagents can be prepared from commercially available reagents:

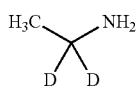

24c

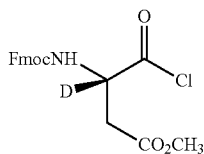

14a

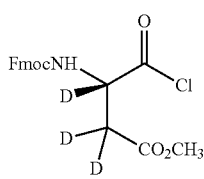

14b

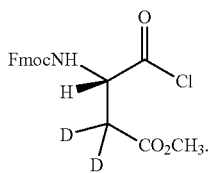

14c

The preparation of intermediate 24c is shown in Scheme 3, below, and is based upon chemistry in Raffery, M. J. et al., Aus. J. Org. Chem., 1988, 41(9), pp. 1477-1489. The preparation of intermediate 14a is described in Rose, J. E. et al., J. Chem. Soc., Perkin Trans. 1, 1995, 2, pp. 157-165. Intermediates 14b and 14c may be prepared in a manner analogous to that used for the preparation of 14a, using readily available deuterated starting materials, such as 2,2-d2-bromoethylacetate (commercially available at 98% d), d1-methanol or d1-ethanol (both commercially available at 98% d).

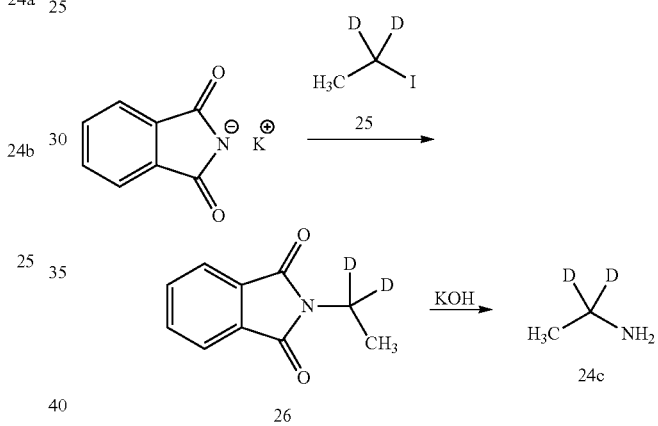

Scheme 3. Synthesis of 24c

Intermediate 24c may be prepared from 2,2-d2-ethyl iodide (commercially available at 99.5% deuterium incorporation) as referenced above.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., R$^1$, R$^2$, R$^3$, etc.) or not. The suitability of a chemical group in a compound structure for use in the synthesis of another compound is within the knowledge of one of ordinary skill in the art.

Additional methods of synthesizing compounds of Formula I and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene, T W et al., *Protective Groups in Organic Synthesis*, 3$^{rd}$ Ed., John Wiley and Sons (1999); Fieser, L et al., *Fieser and Fieser's Reagents for Organic Synthesis*, John Wiley and Sons (1994); and Paquette, L., ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pyrogen-free pharmaceutical compositions comprising an effective amount of a compound of Formula I (e.g., including any of the formulae herein), or a pharmaceutically acceptable salt of said compound; and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

In another embodiment, a composition of this invention further comprises a second therapeutic agent. The second therapeutic agent may be selected from any compound or therapeutic agent known to have or that demonstrates advantageous properties when administered with a compound having the same mechanism of action as I-BET762. Such agents include those indicated as being useful in combination with I-BET762, including but not limited to, those described in US2012220573.

Preferably, the second therapeutic agent is an agent useful in the treatment of a disease or condition selected from neoplasia, inflammatory disease, autoimmune disorders, obesity, fatty liver, diabetes, atherosclerosis, arterial stent occlusion, heart failure, cachexia, graft versus host disease, infectious diseases associated with bromodomains, parasitic infection, malaria, trypanosomes and for reducing male fertility.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat the target disorder.

The interrelationship of dosages for animals and humans (based on milligrams per meter squared of body surface) is described in Freireich et al., Cancer Chemother. Rep, 1966, 50: 219. Body surface area may be approximately determined from height and weight of the subject. See, e.g., Scientific Tables, Geigy Pharmaceuticals, Ardsley, N.Y., 1970, 537.

In one embodiment, an effective amount of a compound of this invention over a course of treatment can range from 0.05 to 1000 mg and may be administered from once to four times per day. In certain aspects of this embodiment, an effective amount of a compound of this invention can range from 0.1 to 1000 mg, 0.1 to 500 mg, 0.1 to 50 mg, 0.5 to 500 mg, 0.5 to 100 mg, 0.5 to 50 mg, 0.5 to 5 mg, 1 to 250 mg, 1 to 100 mg, 1 to 10 mg, 5 to 100 mg, 5 to 50 mg and 5 to 10 mg. In certain aspects of this embodiment the compound may be administered three times a day, twice a day, once a day, or once every other day, over the course of treatment.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician. For example, guidance for selecting an effective dose can be determined by reference to the prescribing information for I-BET762.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of bromodomain inhibition in a cell, comprising contacting a cell with one or more compounds of Formula I herein, or a pharmaceutically acceptable salt thereof.

According to another embodiment, the invention provides a method of treating a disease that is beneficially treated by I-BET762 in a subject in need thereof, comprising the step of administering to the subject an effective amount of a compound or a composition of this invention. In one embodiment the subject is a patient in need of such treatment. Such diseases are well known in the art and are disclosed in, but not limited to, the following patents and published applications: US2012220573 and US 2012252781. Such diseases include, but are not limited to, neoplasia, acute and chronic inflammatory disease, autoimmune disorders, obesity, fatty liver, diabetes, atherosclerosis, arterial stent occlusion, heart failure, cachexia, graft versus host disease, infectious diseases associated with bromodomains, parasitic infection, malaria, trypanosomes and for reducing male fertility.

In one embodiment, chronic autoimmune and inflammatory conditions include conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes and acute rejection of transplanted organs.

In one embodiment, acute inflammatory conditions include conditions such as acute gout, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis and acute rejection of transplanted organs.

In one embodiment, the invention provides a method of treatment of diseases or conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria, SIRS associated with viral infections such as influenza, herpes zoster, herpes simplex and coronavirus.

In one embodiment, the invention provides a method of treatment of diseases or conditions associated with ischaemia-reperfusion injury such as myocardial infarction, cerebrovascular ischaemia (stroke), acute coronary syndromes, renal reperfusion injury, organ transplantation, coronary artery bypass grafting, cardio-pulmonary bypass procedures and pulmonary, renal, hepatic, gastro-intestinal or peripheral limb embolism.

In one embodiment, the invention provides a method of treatment of disorders of lipid metabolism via the regulation of APO-A1 such as hypercholesterolemia, atherosclerosis and Alzheimer's disease.

In one embodiment, the invention provides a method of treatment of fibrotic conditions such as idiopathic pulmonary fibrosis, renal fibrosis, post-operative stricture, keloid formation, scleroderma and cardiac fibrosis.

In one embodiment, the invention provides a method of treatment of viral infections such as herpes virus, human papilloma virus, adenovirus, poxvirus and other DNA viruses.

In one embodiment, the invention provides a method of treatment of cancer, including hematological, epithelial including lung, breast and colon carcinomas, midline carcinomas, mesenchymal, hepatic, renal and neurological tumors.

In one embodiment, the invention provides a method of treating a disease associated with systemic inflammatory response syndrome, such as sepsis, sepsis syndrome, septic shock, endotoxaemia, burns, pancreatitis, acute pancreatitis, chronic pancreatitis, major trauma, haemorrhage and ischaemia.

In one embodiment, the invention provides a method of treating a disease or condition selected from herpes simplex infections and reactivations, cold sores, herpes zoster infections and reactivations, chickenpox, shingles, human papilloma virus, cervical neoplasia, adenovirus infections, including acute respiratory disease, poxvirus infections such as cowpox and smallpox and African swine fever virus, and human papilloma virus infections of skin or cervical epithelia.

In one embodiment, the invention provides a method of treatment of cancer, such as midline carcinoma.

In one embodiment, this invention provides a method of treatment of a disease or condition selected from carcinoma and hematologic cancer in a subject in need thereof.

In one embodiment, the method of this invention is used to treat a disease or condition selected from chronic autoimmune disease and chronic inflammatory disease in a subject in need thereof.

Identifying a subject in need of such treatment can be in the judgment of a subject or a health care professional and can be subjective (e.g. opinion) or objective (e.g. measurable by a test or diagnostic method).

In another embodiment, any of the above methods of treatment comprises the further step of co-administering to the subject in need thereof one or more second therapeutic agents. The choice of second therapeutic agent may be made from any second therapeutic agent known to be useful for co-administration with I-BET762. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I alone or together with one or more of the above-described second therapeutic agents in the manufacture of a medicament, either as a single composition or as separate dosage forms, for treatment in a subject of a disease, disorder or symptom set forth above. Another aspect of the invention is a compound of Formula I for use in the treatment in a subject of a disease, disorder or symptom thereof delineated herein.

EXAMPLES
Example 1. (S)-2-(6-(4-Chlorophenyl)-8-(methoxy-d3)-1-methyl-4H-benzo[f][1,2,4]triazolo[4,3-a][1,4]diazepin-4-yl)-N-ethylacetamide (Compound 104)
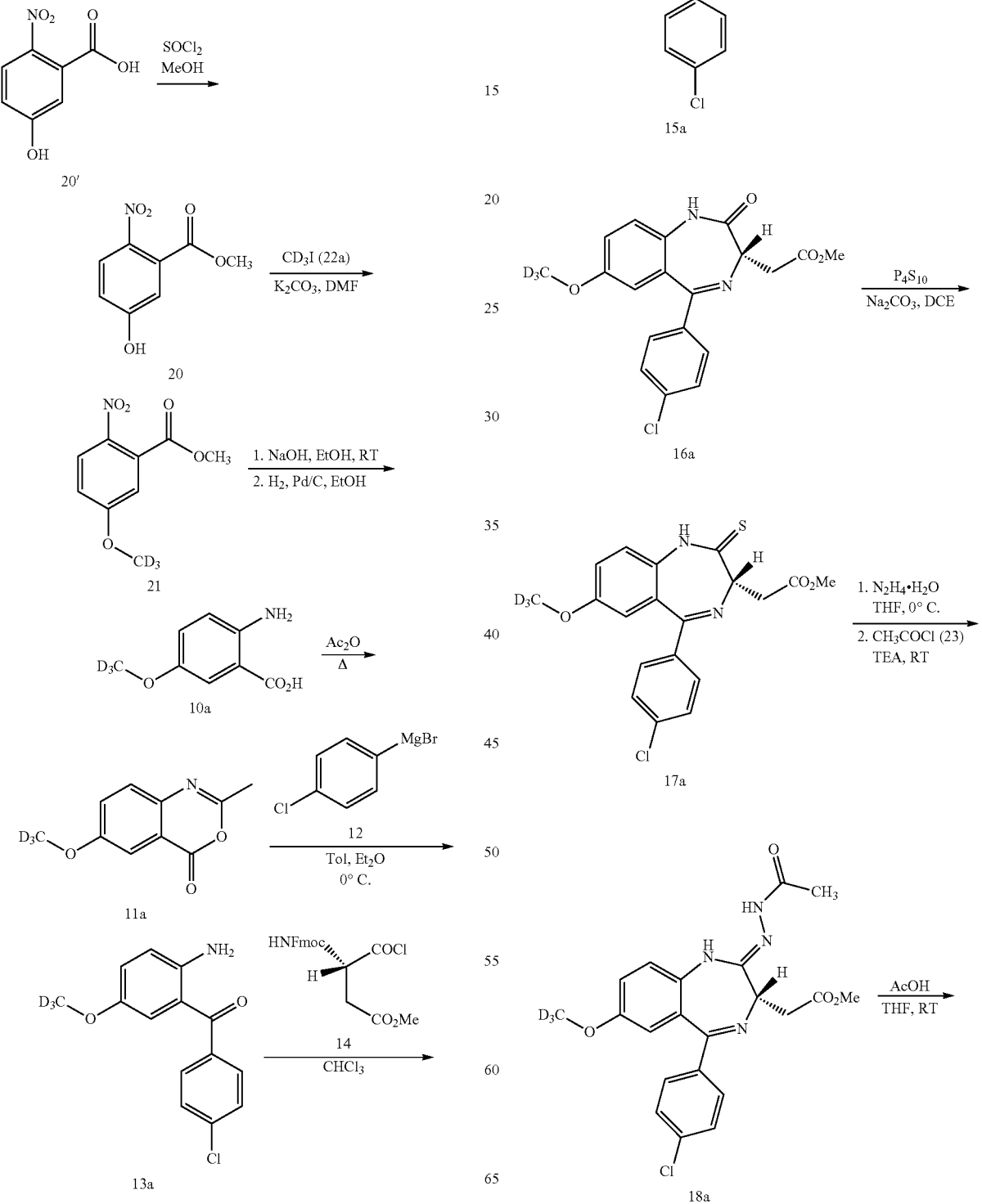

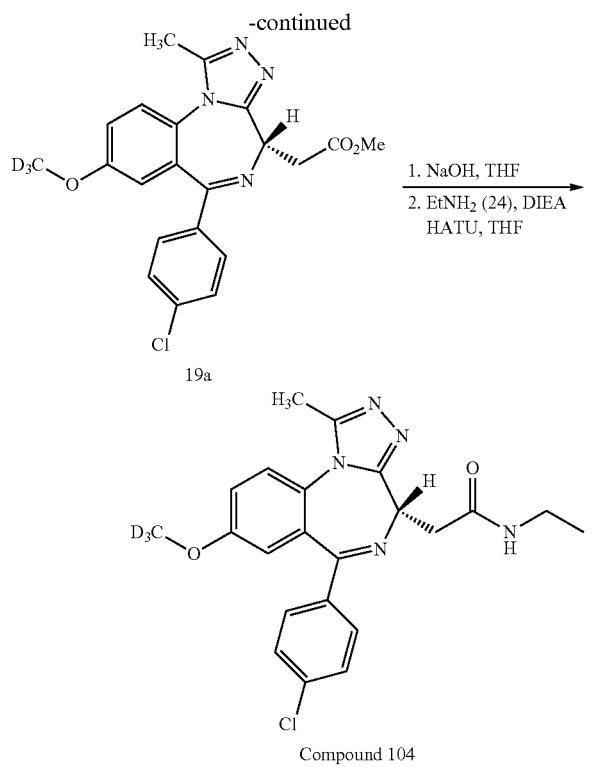

19a

Compound 104

Step 1. Methyl 5-hydroxy-2-nitrobenzoate (20)

Thionyl chloride (13.0 g, 109 mmol) was added slowly at room temperature to a solution of 3-hydroxy-5-nitrobenzoic acid (20') (20.0 g, 109 mmol) in methanol (500 mL). The reaction was heated at reflux for 3 hours, cooled to room temperature and concentrated under reduced pressure. The residue was dissolved in ethyl acetate (200 mL), washed with saturated sodium bicarbonate (200 mL) and saturated sodium chloride (200 mL). The organic layer was dried over sodium sulfate, filtered and concentrated to afford (20) as a white solid (16 g, 74%).

Step 2. Methyl 5-(methoxy-d₃)-2-nitrobenzoate (21)

To a solution of 20 (16 g, 81.2 mmol) in anhydrous DMF (500 mL) was added potassium carbonate (22.4 g, 162.4 mmol), followed by methyl iodide-d₃ (22a), (Cambridge Isotope, 99.5% D) (15.8 g, 106 mmol). The reaction was stirred for 24 hours, cooled to 0° C. and water (3 L) was added slowly over 1 hour. The mixture was extracted with ethyl acetate (3×500 mL). The organic layer was washed with saturated sodium bicarbonate (500 mL), water (2×500 mL), saturated sodium chloride (500 mL), dried over sodium sulfate, filtered and concentrated under reduced pressure. The residue was triturated with 10% ethyl acetate in heptanes to afford (21) as an off-white solid (15 g, 86%).

Step 3. 2-Amino-5-(methoxy-d₃) benzoic acid (10a)

To a solution of 21 (15 g, 70.1 mmol) in THF (200 mL) was added 1N sodium hydroxide (210 mL, 210 mmol). The reaction was stirred 4 hours at room temperature, cooled to 0° C. and adjusted to pH 2 with 3N hydrochloric acid. The resulting mixture was extracted with dichloromethane (3×200 mL) and combined organic phase was dried over sodium sulfate, filtered and concentrated to give the free acid (15 g). The acid was hydrogenated with 10% palladium on carbon (1.3 g; 50 wt % water) in methanol (300 mL) at 35 psi for 6 hours at room temperature. The mixture was filtered through a pad of celite and the filtrate was concentrated to afford 10a as a tan solid (10 g, 85%).

Step 4. 6-(Methoxy-d₃)-2-methyl-4H-benzo[d][1,3]oxazin-4-one (11a)

Compound (10a) (10 g, 60 mmol) was dissolved in acetic anhydride (60 mL) and heated at reflux for 6 hours and concentrated under reduced pressure. The residue was co-evaporated with toluene (3×50 mL), and suspended in MTBE (100 mL), stirred for 15 minutes, and filtered to afford 11a as a brown solid which was taken directly to the next step (9.5 g, 79%).

Step 5. (2-Amino-5-(methoxy-d₃)phenyl)(4-chlorophenyl)methanone (13a)

To a solution of 11a (9.5 g, 49 mmol) in a mixture of toluene and diethyl ether (3:1) (120 mL) at 0° C. was added a solution of 1.0 M 4-chlorophenylmagnesium bromide (12) in methylTHF (40 mL, 40 mmol) over 30 minutes. The reaction was stirred at room temperature for 1 hour, cooled to 0° C. and 1N HCl (50 mL) added. The aqueous layer was extracted with ethyl acetate (2×100 mL), and the organic layer was washed with saturated sodium chloride (100 mL), dried over sodium sulfate, filtered and concentrated under reduced pressure. The residual material was dissolved in ethanol (100 mL) and 6N HCl (30 mL) was added, heated at reflux for 2 hours then concentrated under reduced pressure. The residue was suspended in ethyl acetate (200 mL) and adjusted with 1N NaOH to pH 8-9. The mixture was extracted with ethyl acetate (3×100 mL) and organic layer, washed with saturated sodium chloride (2×200 mL), dried over sodium sulfate and concentrated to afford 13a as a yellow solid (7 g, 54%).

Step 6. Methyl (S)-3-((((9H-fluoren-9-yl)methoxy)carbonyl)amino)-4-((2-(4-chlorobenzoyl)-4-(methoxy-d₃)phenyl)amino)-4-oxobutanoate (15a)

To a solution of Fmoc-Asp (OMe)-OH (10.7 g, 29.2 mmol) in dichloromethane (20 mL) was added thionyl chloride (20 mL), carefully followed by dimethylformamide (0.25 mL, 3.25 mmol). The mixture was stirred at room temperature for 3 hours, concentrated under reduced pressure and the residual material was co-evaporated with toluene (3×100 mL) to give crude 14 (12.3 g). The crude solid was suspended in dichloromethane (100 mL) and 13a (7 g, 26.5 mmol) was added. The reaction was stirred at 60° C. for 2 hours and concentrated to afford 15a as a white solid (14 g, 86%).

Step 7. Methyl (S)-2-(5-(4-chlorophenyl)-7-(methoxy-d₃)-2-oxo-2,3-dihydro-1H-benzo[e][1,4]diazepin-3-yl)acetate (16a)

To a solution of 15a (14 g, 22.7 mmol) in dichloromethane (50 mL) was added triethylamine (57 mL, 409 mmol). The reaction was heated at reflux overnight, concentrated under reduced pressure and the residual material was suspended in 1,2-dichloroethane (130 mL), and acetic acid (13 mL, 227 mmol) was added. The reaction was stirred at 60° C. for 2 hours, concentrated under reduced pressure and the residue was suspended in dichloromethane (300 mL), washed with 1N HCl (100 mL), water (2×100 mL), saturated sodium chloride (100 mL), dried over sodium sulfate, filtered, and concentrated under reduced pressure. The residual material was suspended in acetonitrile (15 mL), stirred for 45 minutes, and the resulting solid was filtered, dried in a vacuum oven at 40° C. overnight to afford 16a as a light brown solid (7.4 g, 87%).

Step 8. Methyl (S)-2-(5-(4-chlorophenyl)-7-(methoxy-d$_3$)-2-thioxo-2,3-dihydro-1H-benzo[e][1,4]diazepin-3-yl)acetate (17a)

Phosphorus pentasulfide (11 g, 24 mmol) was suspended in 1, 2-dichloroethane (150 mL) and sodium carbonate (2.6 g, 24 mmol) was added. The resulting mixture was stirred at room temperature for 1 hour and 16a (5 g, 13.4 mmol) was added. The reaction was stirred at 65° C. for 4 hours, cooled to ambient temperature and filtered. The filtrate was washed with saturated sodium bicarbonate (100 mL), saturated sodium chloride (100 mL), dried over sodium sulfate, filtered, and concentrated under reduced pressure. The crude material was purified using an Analogix automated chromatography system, eluting with a gradient of ethyl acetate in heptanes (0 to 30%). Product fractions were pooled and evaporated yielding 17a as a light yellow solid (3.2 g, 61.2%).

Step 9. Methyl (S,Z)-2-(2-(2-acetylhydrazono)-5-(4-chlorophenyl)-7-(methoxy-d$_3$)-2,3-dihydro-1H-benzo[e][1,4]diazepin-3-yl)acetate (18a)

To a solution of 17a (1.5 g, 3.85 mmol) in THF (60 mL), at 0° C. was added Hydrazine monohydrate (0.56 mL, 12.5 mmol) and the reaction stirred at 0° C. for 4 hours. Triethylamine (1.6 mL, 13.5 mmol) was added, followed by acetyl chloride 23, (1.64 mL, 12.5 mmol) and the reaction was stirred at room temperature for 1 hour, diluted with water (50 mL) and THF was removed under reduced pressure. The resulting residue was extracted with dichloromethane (100 mL) and the organic layer was washed with saturated sodium chloride (100 mL), dried over sodium sulfate, filtered, and concentrated to afford 18a as a yellow solid (1.6 g, 96%).

Step 10. Methyl (S)-2-(6-(4-chlorophenyl)-8-(methoxy-d3)-1-methyl-4H-benzo[f][1,2,4]triazolo[4,3-a][1,4]diazepin-4-yl)acetate (19a)

To a solution of 18a (1.6 g, 3.7 mmol) in THF (50 mL) was added acetic acid (50 mL) and the reaction was stirred at room temperature for 18 hours. The mixture was concentrated under reduced pressure to afford a residue which was dissolved in dichloromethane (100 mL), washed with saturated sodium bicarbonate (3×50 mL), water (100 mL), saturated sodium chloride (100 mL), and dried over sodium sulfate, filtered, and concentrated under reduced pressure. The crude material was purified using an Analogix automated chromatography system, eluting with methanol in dichloromethane (0 to 5%). Product fractions were pooled and evaporated to afford 19a as a light yellow solid (1.2 g, 82%).

Step 11. (S)-2-(6-(4-Chlorophenyl)-8-(methoxy-d$_3$)-1-methyl-4H-benzo[f][1,2,4]triazolo[4,3-a][1,4]diazepin-4-yl)-N-ethylacetamide (Compound 104)

To a solution of 19a (1.2 g, 2.9 mmol) in THF (20 mL) was added 1N NaOH (8.7 mL, 8.7 mmol). The reaction was stirred for 6 hours at room temperature, cooled to 0° C. and adjusted with 1N HCl to pH 4. The resulting mixture was extracted with dichloromethane (3×50 mL) and the combined organic layer was dried over sodium sulfate, filtered, and concentrated to give the free acid as a yellow solid (1.0 g, 86%). To a solution of the free acid (500 mg, 1.25 mmol) in THF (20 mL) was added HATU (950 mg, 2.5 mmol), followed by diisopropylethylamine (0.42 mL, 2.5 mmol) and the reaction was stirred at room temperature for 3 hours. Ethylamine hydrochloride (24) (200 mg, 2.5 mmol) was added, followed by diisopropylethylamine (0.42 mL, 2.5 mmol) and the reaction was stirred at room temperature for 18 hours. The resulting mixture was concentrated under reduced pressure and the residual material was dissolved in a mixture of water (30 mL) and dichloromethane (30 mL), stirred for 30 minutes and extracted with dichloromethane (2×50 mL). The combined organic phase was washed with water (2×100 mL), saturated sodium chloride (100 mL), dried over sodium sulfate, filtered and concentrated under reduced pressure. The residual material was purified using an Analogix automated chromatography system eluting with methanol in dichloromethane (0 to 5%). Product fractions were pooled and evaporated to give a material with enantiomeric purity of 94% ee (400 mg). The material was further purified using chiral preparative HPLC (20×250 mm, 10 μm column, Daicel ChiralPak AD, eluting with 80% isopropanol/20% hexane at a flow rate of 17 mL/min). Product fractions were pooled and evaporated to afford 104 as an off white solid (280 mg, 53%). $^1$H-NMR (300 MHz, CDCl$_3$): δ 1.18 (m, 3H), 2.61 (s, 3H), 3.24-3.35 (m, 2H), 3.36-3.41 (m, 1H), 3.47-3.54 (m, 1H), 4.61 (t, J=7 Hz, 1H), 6.4 (bm, 1H), 6.85 (m, 1H), 7.17-7.21 (m, 1H), 7.32-7.35 (m, 2H), 7.36 (s, 1H), 7.46-7.51 (m, 2H); $^{13}$C-NMR (75 MHz, CDCl$_3$): δ 12.12, 14.78, 34.49, 39.47, 53.93, 115.79, 117.93, 124.81, 126.44, 128.49, 130.12, 130.73, 137.94, 137.14, 150.46, 156.43, 157.98, 166.20, 170.3. MS(ESI) [(M+H)$^+$] C$_{22}$H$_{19}$D$_3$ClN$_5$O$_2$: 427; HPLC (method: SorbTech C18AQ, 2.1×50 mm 3 μm column-gradient method 5-95% ACN+ 0.1% formic acid in 14 min with 4 min hold at 95% ACN+0.1% formic acid; Wavelength: 254 nm): retention time: 6.33 min; 99.1% purity; Chiral HPLC (method: 25 cm×4.6 mm, 10 μm column Chiralpak AD, isocratic method 40% heptane +60% EtOH for 30 minutes at 1.0 mL/min, Wavelength: 210 nm): retention time: 4.654 min, purity: 97.87% ee.

Example 2. S)-2-(6-(4-Chlorophenyl)-8-methoxy-1-(methyl-d3)-4H-benzo[f][1,2,4]triazolo[4,3-a][1,4]diazepin-4-yl)-N-ethylacetamide (Compound 105)

Scheme 5: Preparation of Compound 105

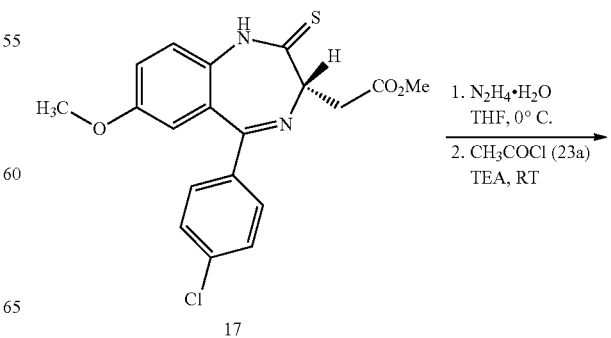

17

-continued

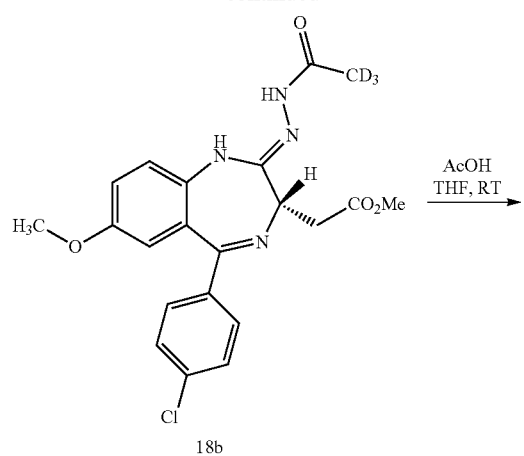

18b

19b

Compound 105

Step 1. Methyl (S,Z)-2-(2-(2-(acetyl-d₃)hydrazono)-5-(4-chlorophenyl)-7-methoxy-2,3-dihydro-1H-benzo[e][1,4]diazepin-3-yl)acetate (18b)

To a solution of 17 (1 g, 2.6 mmol) in THF (50 mL) at 0° C. was added Hydrazine monohydrate (0.38 mL, 8 mmol) and the reaction was stirred at 0° C. for 4 hours. Triethylamine (1.1 mL, 7.8 mmol) was added, followed by the addition of acetyl chloride-d₃ (23a) (0.6 mL, 8 mmol, Cambridge Isotopes, 98% D) and the reaction was stirred at room temperature for 1 hour, diluted with water (50 mL) and the THF was removed under reduced pressure. The residual material was extracted with dichloromethane (1×100 mL), washed with saturated sodium chloride (100 mL), dried over sodium sulfate, filtered, and concentrated to afford 18b as a brown solid (1.1 g, 99%).

Step 2. Methyl (S)-2-(6-(4-chlorophenyl)-8-methoxy-1-(methyl-d₃)-4H-benzo[f][1,2,4]triazolo[4,3-a][1,4]diazepin-4-yl)acetate (19b)

To a solution of 18b (1.1 g, 2.55 mmol) in THF (40 mL) was added acetic acid (40 mL) and the reaction was stirred at room temperature for 18 hours. The resulting mixture was concentrated under reduced pressure to afford a residue which was dissolved in dichloromethane (150 mL), washed with saturated sodium bicarbonate (3×50 mL), water (100 mL), saturated sodium chloride (100 mL), and dried over sodium sulfate, filtered, and concentrated under reduced pressure. The crude material was purified using an Analogix automated chromatography system, eluting with methanol in dichloromethane (0 to 5%). Product fractions were pooled and evaporated to afford 19b as a light yellow solid (0.96 g, 91%).

Step 3. (S)-2-(6-(4-Chlorophenyl)-8-methoxy-1-(methyl-d₃)-4H-benzo[f][1,2,4]triazolo[4,3-a][1,4]diazepin-4-yl)-N-ethylacetamide (Compound 105)

To a solution of 19b (0.96 g, 2.33 mmol) in THF (20 mL) was added 1N NaOH (7 mL, 7 mmol) and the reaction was stirred for 5 hours at 40° C., cooled to 0° C. and adjusted with 1N HCl solution to pH 4-5. The resulting mixture was extracted with dichloromethane (3×50 mL), and the combined organic layer was dried over sodium sulfate, filtered, and concentrated to give the free acid as a yellow solid (940 mg, 100%). To a solution of the free acid (460 mg, 1.15 mmol) in THF (20 mL) was added HATU (880 mg, 2.31 mmol), followed by diisopropylethylamine (0.4 mL, 2.31 mmol) and the reaction was stirred at room temperature for 3 hours. Ethylamine hydrochloride (24) (188 mg, 2.31 mmol) was added, followed by diisopropylethylamine (0.4 mL, 2.31 mmol) and the reaction was stirred at room temperature for 18 hours. The resulting mixture was concentrated under reduced pressure and the residual material was dissolved in a mixture of water (30 mL) and dichloromethane (30 mL), stirred for 30 minutes and extracted with dichloromethane (2×50 mL). The combined organic phase was washed with water (2×100 mL), saturated sodium chloride (100 mL), dried over sodium sulfate, filtered and concentrated under reduced pressure. The residual material was purified using an Analogix automated chromatography system eluting with methanol in dichloromethane (0 to 5%). Product fractions were pooled and evaporated to give a material with enantiomeric purity of 88% ee (380 mg). The material was further purified using chiral preparative HPLC (20×250 mm, 10 μm column, Daicel ChiralPak AD, eluting with 80% isopropanol/20% hexane at a flow rate of 17 mL/min). Product fractions were pooled and evaporated to afford (105) as an off white solid (240 mg, 49%). $^1$H-NMR (300 MHz, CDCl₃): δ 1.18 (t, J=7.3 Hz, 3H), 3.23-3.34 (m, 2H), 3.35-3.3.55 (m, 2H), 3.8 (s, 3H), 4.62 (t, J=7 Hz, 1H), 6.43 (bm, 1H), 6.85 (d, J=2.7 Hz, 1H), 7.18-7.22 (m, 1H), 7.27-7.34 (m, 2H), 7.35, (s, 1H), 7.47-7.51 (m, 2H); $^{13}$C-NMR (75 MHz, CDCl₃): δ 14.78, 34.49, 39.46, 53.92, 55.86, 115.81, 117.94, 124.78, 126.47, 128.49, 130.10, 130.74, 136.94, 137.15, 156.43, 157.97, 166.18, 170.30. MS(ESI) [(M+H)⁺] $C_{22}H_{19}D_3ClN_5O_2$: 427; HPLC (method: SorbTech C18AQ, 2.1×50 mm 3 μm column-gradient method 5-95% ACN+0.1% formic acid in 14 min with 4 min hold at 95% ACN+0.1% formic acid; Wavelength: 254 nm): retention time: 6.353 min; 98% purity; Chiral HPLC (method: 25 cm×4.6 mm, 10 μm column Chiralpak AD,

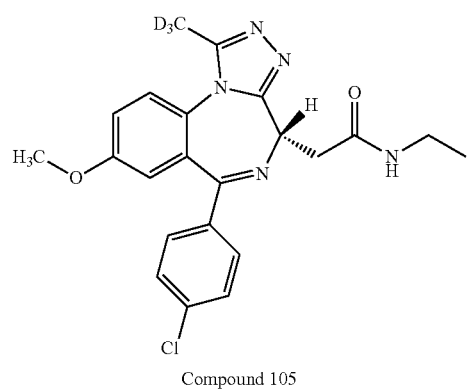

isocratic method 40% heptane +60% EtOH for 30 minutes at 1.0 mL/min, Wavelength: 210 nm): retention time: 4.650 min, purity: 96.91% ee.

Example 3. (S)-2-(6-(4-chlorophenyl)-8-methoxy-1-methyl-4H-benzo[f][1,2,4]triazolo[4,3-a][1,4]diazepin-4-yl)-N-(ethyl-d5)acetamide (Compound 101)

Scheme 6: Preparation of Compound 101

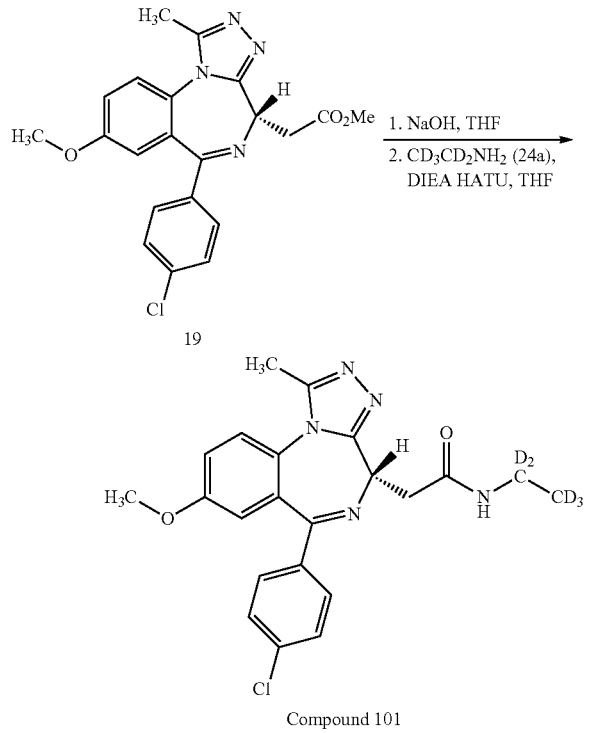

Compound 101

(S)-2-(6-(4-chlorophenyl)-8-methoxy-1-methyl-4H-benzo[f][1,2,4]triazolo[4,3-a][1,4]diazepin-4-yl)-N-(ethyl-d₅)acetamide (Compound 101)

To a solution of the free acid of 19 (400 mg, 1.01 mmol) (prepared by treating with 1N NaOH/THF as described in step 3 of 105) was dissolved in THF (20 mL) and HATU (768 mg, 2.02 mmol) was added, followed by diisopropylethylamine (0.34 mL, 2.02 mmol) and the reaction was stirred for 3 hours at room temperature. Ethylamine hydrochloride-d₅ (24a) (165 mg, 2.02 mmol, Sigma Aldrich, 99% D) was added, followed immediately by diisopropylethylamine (0.34 mL, 2.02 mmol) and the reaction was stirred at room temperature for 18 hours. The resulting mixture was concentrated under reduced pressure and the residual material was dissolved in a mixture of water (30 mL) and dichloromethane (30 mL), stirred for 30 minutes and extracted with dichloromethane (2×50 mL). The combined organic phase was washed with water (2×100 mL), saturated sodium chloride (100 mL), dried over sodium sulfate, filtered and concentrated under reduced pressure. The residual material was purified using an Analogix automated chromatography system eluting with methanol in dichloromethane (0 to 5%). Product fractions were pooled and evaporated to give a material with enantiomeric purity of 88% ee (350 mg). The material was further purified using chiral preparative HPLC (20×250 mm, 10 μm column, Daicel ChiralPak AD, eluting with 80% isopropanol/20% hexane at a flow rate of 17 mL/min). Product fractions were pooled and evaporated to afford (101) as an off white solid (210 mg, 48%). $^1$H-NMR (300 MHz, CDCl$_3$): δ 2.61 (s, 3H), 3.29-3.36 (m, 1H), 3.47-3.54 (m, 1H), 3.80 (s, 3), 4.61 (t, J=7 Hz, 1H), 6.35 (bm, 1H), 6.85-6.86 (d, J=2.9 Hz, 1H), 7.17-7.21 (m, 1H), 7.22-7.34 (m, 2H), 7.36, (s, 1H), 7.43-7.5 (m, 2H); $^{13}$C-NMR (75 MHz, CDCl$_3$): δ 12.13, 39.49, 53.93, 55.87, 115.81, 117.94, 124.80, 126.46, 128.50, 130.11, 130.73, 136.95, 137.14, 150.46, 156.42, 157.98, 166.19, 170.32; MS(ESI) [(M+H)$^+$] C$_{22}$H$_{17}$D$_5$ClN$_5$O$_2$: 429; HPLC (method: SorbTech C18AQ, 2.1×50 mm 3 μm column-gradient method 5-95% ACN+0.1% formic acid in 14 min with 4 min hold at 95% ACN+0.1% formic acid; Wavelength: 254 nm): retention time: 6.341 min; 98.6% purity; Chiral HPLC (method: 25 cm×4.6 mm, 10 μm column Chiralpak AD, isocratic method 40% heptane +60% EtOH for 30 minutes at 1.0 mL/min, Wavelength: 210 nm): retention time: 4.650 min, purity: 99.14% ee.

Example 4. (S)-2-(6-(4-Chlorophenyl)-8-(methoxy-d₃)-1-(methyl-d₃)-4H benzo[f][1,2,4]triazolo[4,3-a][1,4]diazepin-4-yl)-N-ethylacetamide (Compound 112)

Scheme 7: Preparation of Compound 112

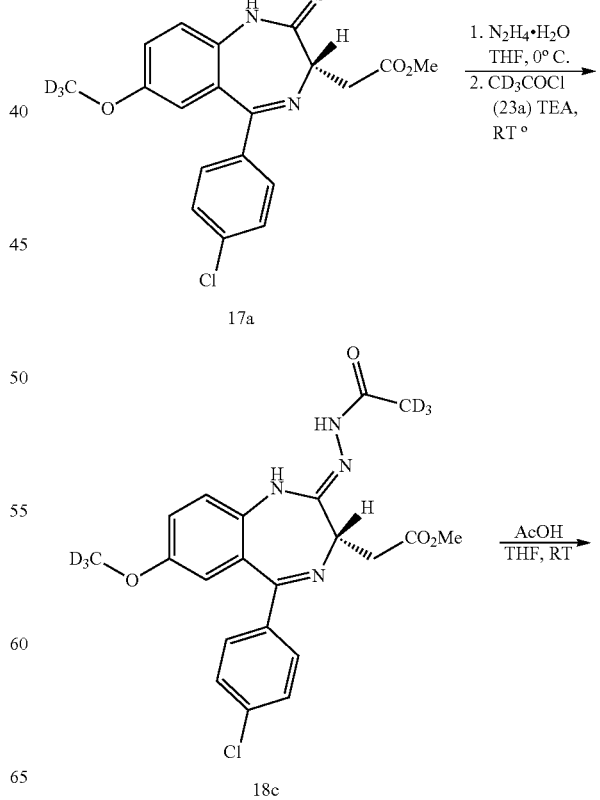

-continued

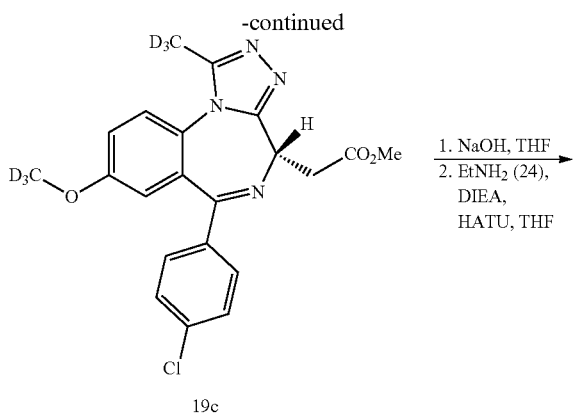

19c

1. NaOH, THF
2. EtNH$_2$ (24), DIEA, HATU, THF

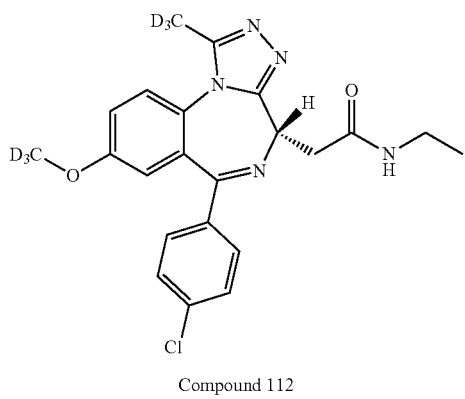

Compound 112

Step 1. Methyl (S,Z)-2-(2-(2-(acetyl-d$_3$)hydrazono)-5-(4-chlorophenyl)-7-(methoxy-d$_3$)-2,3-dihydro-1H-benzo[e][1,4]diazepin-3-yl)acetate (18c)

To a solution of 17a (1.2 g, 3.07 mmol) in THF (50 mL) at 0° C. was added Hydrazine monohydrate (0.44 mL, 9.3 mmol). The reaction was stirred at 0° C. for 4 hours and triethylamine (1.3 mL, 9.3 mmol) was added, followed by acetyl chloride-d$_3$ (23a) (0.7 mL, 9.3 mmol, Cambridge Isotopes, 98% D). The reaction was stirred at room temperature for 1 hour, diluted with water (50 mL) and THF was removed under reduced pressure. The resulting residue was extracted with dichloromethane (100 mL), washed with saturated sodium chloride (100 mL), dried over sodium sulfate, filtered, and concentrated to give crude titled compound (18c) as a brown solid (1.5 g, 99%).

Step 2. Methyl (S)-2-(6-(4-chlorophenyl)-8-(methoxy-d$_3$)-1-(methyl-d$_3$)-4H-benzo[f][1,2,4]-triazolo[4,3-a][1,4]diazepin-4-yl)acetate (19c)

To a solution of 18c (1.5 g, 3.07 mmol) in THF (40 mL) was added acetic acid (40 mL) and the reaction was stirred at room temperature for 18 h. The mixture was concentrated under reduced pressure to afford a residue which was dissolved in dichloromethane (150 mL), washed with saturated sodium bicarbonate solution (3×50 mL), water (100 mL) and saturated sodium chloride (100 mL), dried over sodium sulfate, filtered, and concentrated under reduced pressure. The residual material was purified using an Analogix automated chromatography system eluting with methanol in dichloromethane (0 to 5%). Product fractions were pooled and evaporated to afford 19c as a light yellow solid (1.1 g, 85%).

Step 3. (S)-2-(6-(4-Chlorophenyl)-8-(methoxy-d$_3$)-1-(methyl-d$_3$)-4H-benzo[f][1,2,4]triazolo[4,3-a][1,4]diazepin-4-yl)-N-ethylacetamide (Compound 112)

To a solution of 19c (1.1 g, 2.55 mmol) in THF (20 mL) was added 1N NaOH (7.7 mL, 7.7 mmol). The reaction was stirred for 5 hours at 40° C., cooled to 0° C. and adjusted with 1N HCl solution to pH 4-5. The resulting mixture was extracted with dichloromethane (3×50 mL) and the combined organic layer was dried over sodium sulfate, filtered, and concentrated to give the free acid as a yellow solid (960 mg, 93%). To a solution of the free acid (480 mg, 1.17 mmol) in THF (20 mL) was added HATU (880 mg, 2.34 mmol), followed by diisopropylethylamine (0.4 mL, 2.34 mmol) and the reaction was stirred at room temperature for 3 hours. Ethylamine hydrochloride (24) (190 mg, 2.34 mmol) was added, followed immediately by diisopropylethylamine (0.4 mL, 2.34 mmol) and the reaction was stirred at room temperature for 18 hours. The resulting mixture was concentrated under reduced pressure and the residual material was dissolved in a mixture of water (30 mL) and dichloromethane (30 mL), stirred for 30 minutes and extracted with dichloromethane (2×50 mL). The combined organic phase was washed with water (2×100 mL), saturated sodium chloride (100 mL), dried over sodium sulfate, filtered and concentrated. The crude residue was purified using an Analogix automated chromatography system eluting with methanol in dichloromethane (0 to 5%). Product fractions were pooled and evaporated to give a material with enantiomeric purity of 92% ee (390 mg). The material was further purified using chiral preparative HPLC (method: Daicel ChiralPak AD 20×250 mm, 10 Lm column, eluting with 80% isopropanol/20% hexane at a flow rate of 17 mL/min). Product fractions were pooled and evaporated to afford 112 as an off white solid (240 mg, 49%). $^1$H-NMR (300 MHz, CDCl$_3$): δ 1.18 (m, 3H), 3.23-3.32 (m, 2H), 3.34-3.40 (m, 1H), 3.41-3.54 (m, 1H), 4.62 (t, J=7 Hz, 1H), 6.39 (bm, 1H), 6.85 (d, J=2.9 Hz, 1H), 7.17-7.21 (m, 1H), 7.32-7.34 (m, 2H), 7.35, (s, 1H), 7.46-7.5 (m, 2H); $^{13}$C-NMR (75 MHz, CDCl$_3$): δ 14.78, 34.49, 39.49, 53.93, 115.79, 117.94, 124.79, 126.45, 128.50, 130.11, 130.74, 136.95, 137.15, 156.43, 157.97, 166.19, 170.30. MS(ESI) [(M+H)$^+$] C$_{22}$H$_{16}$D$_6$ClN$_5$O$_2$: 430; HPLC (method: SorbTech C18AQ, 2.1×50 mm 3 μm column-gradient method 5-95% ACN+ 0.1% formic acid in 14 min with 4 min hold at 95% ACN+0.1% formic acid; Wavelength: 254 nm): retention time: 6.314 min; 99.2% purity; Chiral HPLC (method: 25 cm×4.6 mm, 10 μm column Chiralpak AD, isocratic method 40% heptane +60% EtOH for 30 minutes at 1.0 mL/min, Wavelength: 210 nm): retention time: 4.652 min, purity: 98.06% ee.

Example 5. (S)-2-(6-(4-Chlorophenyl)-8-(methoxy-d₃)-1-methyl-4H-benzo[f][1,2,4]triazolo[4,3-a][1,4]diazepin-4-yl)-N-(ethyl-d5)acetamide (Compound 113)

Scheme 8: Preparation of Compound 113

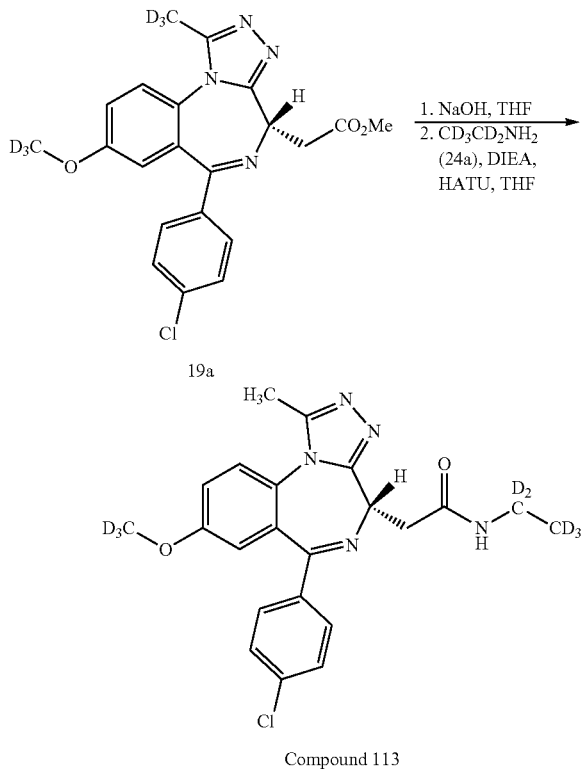

Compound 113

(S)-2-(6-(4-Chlorophenyl)-8-(methoxy-d₃)-1-methyl-4H-benzo[f][1,2,4]triazolo[4,3-a][1,4]diazepin-4-yl)-N-(ethyl-d5)acetamide (Compound 113)

To a solution of the free acid of 19a (500 mg, 1.25 mmol) (prepared by treating with 1N NaOH/THF as described in step 3 of Compound 112) in THF (20 mL) was added HATU (950 mg, 2.5 mmol) followed by diisopropylethylamine (0.42 mL, 2.5 mmol) and the reaction was stirred for 3 hours at room temperature. Ethylamine hydrochloride-d₅ (24a) (220 mg, 2.5 mmol, Sigma Aldrich, 99% D) was added followed by diisopropylethylamine (0.42 mL, 2.5 mmol) and the reaction was stirred at room temperature for 18 hours. The resulting mixture was concentrated under reduced pressure and the residual material was dissolved in a mixture of water (30 mL) and dichloromethane (30 mL), stirred for 30 minutes and extracted with dichloromethane (2×50 mL). The combined organic phase was washed with water (2×100 mL) and saturated sodium chloride (100 mL), dried over sodium sulfate, filtered, and concentrated under reduced pressure. The resulting residue was purified using an Analogix automated chromatography system eluting with methanol in dichloromethane (0 to 5%). Product fractions were pooled and evaporated to give a material with enantiomeric purity of 94% ee (400 mg). The material was further purified using chiral preparative HPLC (Daicel ChiralPak AD 20×250 mm, 10 μm column, eluting with 80% isopropanol/20% hexane at a flow rate of 17 mL/min). Product fractions were pooled and evaporated to afford 113 as an off white solid (280 mg, 51%). $^1$H-NMR (300 MHz, CDCl₃): δ 2.61 (s, 3H), 3.29-3.36 (m, 1H), 3.47-3.54 (m, 1H), 4.61 (t, J=7 Hz, 1H), 6.36 (bm, 1H), 6.85 (d, J=2.9 Hz, 1H), 7.17-7.21 (m, 1H), 7.32-7.35 (m, 2H), 7.36, (s, 1H), 7.46-7.5 (m, 2H); $^{13}$C-NMR (75 MHz, CDCl₃): δ 12.13, 39.49, 115.79, 117.92, 124.81, 126.44, 128.49, 130.12, 130.73, 136.94, 137.15, 150.46, 156.43, 157.98, 166.19, 170.33. MS(ESI) [(M+H)⁺] $C_{22}H_{14}D_8ClN_5O_2$: 432; HPLC (method: SorbTech C18AQ, 2.1×50 mm 3 μm column-gradient method 5-95% ACN+0.1% formic acid in 14 min with 4 min hold at 95% ACN+0.1% formic acid; Wavelength: 254 nm): retention time: 6.301 min; 99.1% purity; Chiral HPLC (method: 25 cm×4.6 mm, 10 μm column Chiralpak AD, isocratic method 40% heptane +60% EtOH for 30 minutes at 1.0 mL/min, Wavelength: 210 nm): retention time: 4.645 min, purity: 98.90% ee.

Example 6. (S)-2-(6-(4-chlorophenyl)-8-methoxy-1-(methyl-d₃)-4H-benzo[f][1,2,4]triazolo[4,3-a][1,4]diazepin-4-yl)-N-(ethyl-d₅)acetamide (Compound 116)

Scheme 9: Preparation of Compound 116

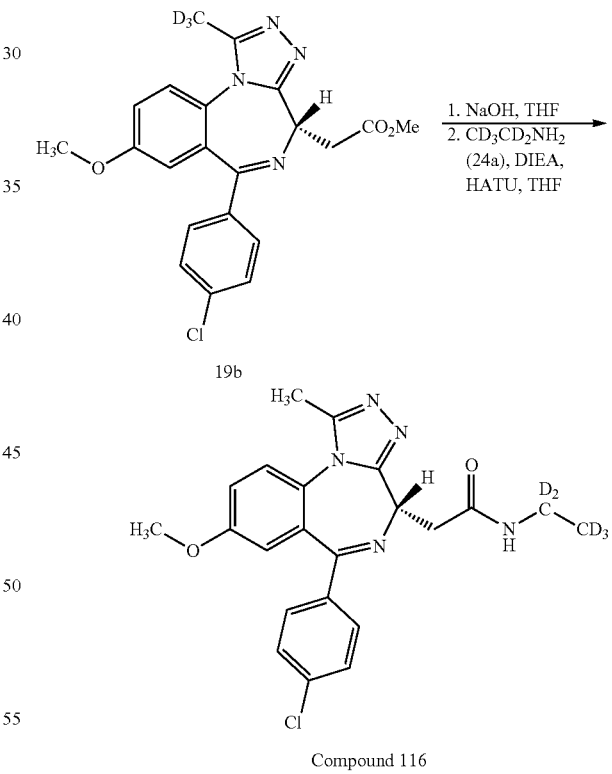

Compound 116

(S)-2-(6-(4-chlorophenyl)-8-methoxy-1-(methyl-d₃)-4H-benzo[f][1,2,4]triazolo[4,3-a][1,4]diazepin-4-yl)-N-(ethyl-d₅)acetamide (Compound 116)

To a solution of the free acid of 19b (500 mg, 1.4 mmol) (prepared by treating with 1N NaOH/THF as described in step 1 of Compound 113) in THF (20 mL) was added HATU (1.06 g, 2.8 mmol) followed by diisopropylethylamine (0.48 mL, 2.8 mmol) and the reaction was stirred at room temperature for 3 hours. Ethylamine hydrochloride-d₅ (24a) (240 mg, 2.8 mmol, Sigma Aldrich, 99% D) was added, followed by and diisopropylethylamine (0.48 mL, 2.5 mmol), and the reaction was stirred at room temperature for 18 hours. The resulting mixture was concentrated under reduced pressure and the residual material was dissolved in a mixture of water (30 mL) and dichloromethane (30 mL), stirred for 30 minutes and extracted with dichloromethane (2×50 mL). The combined organic phase was washed with water (2×100 mL), saturated sodium chloride (100 mL), dried over sodium sulfate, filtered and concentrated. The resulting residue was purified using an Analogix automated chromatography system eluting with methanol in dichloromethane (0 to 5%). Product fractions were pooled and evaporated to give a material with enantiomeric purity of 88% ee (400 mg). The material was further purified using chiral preparative HPLC (Daicel ChiralPak AD, 20×250 mm, 10 μm column, eluting with 80% isopropanol/20% hexane at a flow rate of 17 mL/min). Product fractions were pooled and evaporated to afford 116 as an off white solid (320 mg, 57%). ¹H-NMR (300 MHz, CDCl₃): δ 3.29-3.36 (m, 1H), 3.47-3.54 (m, 1H), 3.8 (s, 3H), 4.61 (t, J=7 Hz, 1H), 6.35 (bm, 1H), 6.86 (d, J=2.9 Hz, 1H), 7.18-7.21 (m, 1H), 7.31-7.35 (m, 2H), 7.36, (s, 1H), 7.46-7.51 (m, 2H); ¹³C-NMR (75 MHz, CDCl₃): δ 39.47, 53.92, 55.87, 115.81, 117.94, 124.78, 126.48, 128.49, 130.11, 130.73, 136.94, 137.15, 156.43, 157.97, 162.61, 166.18, 170.33. MS(ESI) [(M+H)⁺] $C_{22}H_{14}D_8ClN_5O_2$: 432; HPLC (method: SorbTech C18AQ, 2.1×50 mm 3 μm column-gradient method 5-95% ACN+0.1% formic acid in 14 min with 4 min hold at 95% ACN+0.1% formic acid; Wavelength: 254 nm): retention time: 6.343 min; 98.6% purity; Chiral HPLC (method: 25 cm×4.6 mm, 10 μm column Chiralpak AD, isocratic method 40% heptane +60% EtOH for 30 minutes at 1.0 mL/min, Wavelength: 210 nm): retention time: 4.643 min, purity: 97.87% ee.

Example 7. (S)-2-(6-(4-chlorophenyl)-8-(methoxy-d₃)-1-(methyl-d₃)-4H-benzo[f][1,2,4]triazolo[4,3-a][1,4]diazepin-4-yl)-N-ethylacetamide (Compound 126)

Scheme 10: Preparation of Compound 126

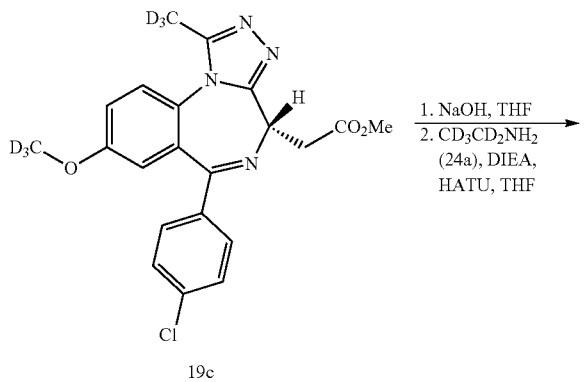

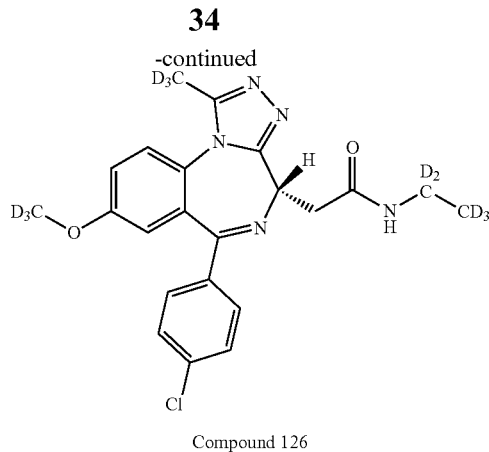

Compound 126

(S)-2-(6-(4-chlorophenyl)-8-(methoxy-d₃)-1-(methyl-d₃)-4H-benzo[f][1,2,4]triazolo[4,3-a][1,4]diazepin-4-yl)-N-ethylacetamide (Compound 126)

To a solution of free acid of 19c (480 mg, 1.17 mmol) (prepared by treating with 1N NaOH/THF as described in step 1 of 116) in THF (20 mL) was added HATU (880 mg, 2.34 mmol, 2.0 equiv) followed by diisopropylethylamine (0.4 mL, 2.34 mmol) and the reaction was stirred at room temperature for 3 hours. Ethylamine hydrochloride-d₅ (24a) (200 mg, 2.34 mmo, Sigma Aldrich, 99% D) was added, followed by diisopropylethylamine (0.4 mL, 2.34 mmol) and the reaction was stirred at room temperature for 18 hours. The resulting mixture was concentrated under reduced pressure and the residual material was dissolved in a mixture of water (30 mL) and dichloromethane (30 mL), stirred for 30 minutes and extracted with dichloromethane (2×50 mL). The combined organic phase was washed with water (2×100 mL), saturated sodium chloride (100 mL), dried over sodium sulfate, filtered and concentrated. The resulting residue was purified using an Analogix automated chromatography system eluting with methanol in dichloromethane (0 to 5%). Product fractions were pooled and evaporated to give a material with enantiomeric purity of 92% ee (380 mg). The material was further purified using chiral preparative HPLC (Daicel ChiralPak AD 20×250 mm, 10 μm column, eluting with 80% isopropanol/20% hexane at a flow rate of 17 mL/min). Product fractions were pooled and evaporated to afford 126 as an off white solid (240 mg, 49%). ¹H-NMR (300 MHz, CDCl₃): δ 3.29-3.36 (m, 1H), 3.47-3.54 (m, 1H), 4.62 (t, J=7 Hz, 1H), 6.41 (bs, 1H), 6.85 (d, J=2.9 Hz, 1H), 7.18-7.22 (m, 1H), 7.27-7.32 (m, 2H), 7.36, (s, 1H), 7.47-7.51 (m, 2H); ¹³C-NMR (75 MHz, CDCl₃): δ 39.46, 53.92, 115.78, 117.96, 124.81, 126.41, 128.52, 130.08, 130.75, 136.94, 137.14, 156.41, 157.97, 166.27, 170.35. MS(ESI) [(M+H)⁺] $C_{22}H_{11}D_{11}ClN_5O_2$: 435; HPLC (method: SorbTech C18AQ, 2.1×50 mm 3 μm column-gradient method 5-95% ACN+0.1% formic acid in 14 min with 4 min hold at 95% ACN+0.1% formic acid; Wavelength: 254 nm): retention time: 6.325 min; 98.6% purity; Chiral HPLC (method: 25 cm×4.6 mm, 10 μm column Chiralpak AD, isocratic method 40% heptane +60% EtOH for 30 minutes at 1.0 mL/min, Wavelength: 210 nm): retention time: 4.644 min, purity: 100% ee.

Example X. Evaluation of Metabolic Stability

Microsomal Assay:

Human liver microsomes (20 mg/mL) are obtained from Xenotech, LLC (Lenexa, Kans.). β-nicotinamide adenine dinucleotide phosphate, reduced form (NADPH), magnesium chloride ($MgCl_2$), and dimethyl sulfoxide (DMSO) are purchased from Sigma-Aldrich.

Determination of Metabolic Stability:

7.5 mM stock solutions of test compounds are prepared in DMSO. The 7.5 mM stock solutions are diluted to 12.5-50 µM in acetonitrile (ACN). The 20 mg/mL human liver microsomes are diluted to 0.625 mg/mL in 0.1 M potassium phosphate buffer, pH 7.4, containing 3 mM $MgCl_2$. The diluted microsomes are added to wells of a 96-well deep-well polypropylene plate in triplicate. A 10 µL aliquot of the 12.5-50 µM test compound is added to the microsomes and the mixture is pre-warmed for 10 minutes. Reactions are initiated by addition of pre-warmed NADPH solution. The final reaction volume is 0.5 mL and contains 0.5 mg/mL human liver microsomes, 0.25-1.0 µM test compound, and 2 mM NADPH in 0.1 M potassium phosphate buffer, pH 7.4, and 3 mM $MgCl_2$. The reaction mixtures are incubated at 37° C., and 50 µL aliquots are removed at 0, 5, 10, 20, and 30 minutes and added to shallow-well 96-well plates which contain 50 µL of ice-cold ACN with internal standard to stop the reactions. The plates are stored at 4° C. for 20 minutes after which 100 µL of water is added to the wells of the plate before centrifugation to pellet precipitated proteins. Supernatants are transferred to another 96-well plate and analyzed for amounts of parent remaining by LC-MS/MS using an Applied Bio-systems API 4000 mass spectrometer. The same procedure is followed for the non-deuterated counterpart of the compound of Formula I and the positive control, 7-ethoxycoumarin (1 µM). Testing is done in triplicate.

Data analysis: The in vitro $t_{1/2}$s for test compounds are calculated from the slopes of the linear regression of % parent remaining (ln) vs incubation time relationship.

$$\text{in vitro } t_{1/2} = 0.693/k$$

$k = -[\text{slope of linear regression of \% parent remaining (ln) vs incubation time}]$ Data analysis is performed using Microsoft Excel Software.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

I claim:

1. A method of treating a subject suffering from a chronic autoimmune or inflammatory condition selected from rheumatoid arthritis, osteoarthritis, acute gout, psoriasis, systemic lupus erythematosus, multiple sclerosis, inflammatory bowel disease, Crohn's disease ulcerative colitis, asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes and acute rejection of transplanted organs, the method comprising a step of administering to the subject in need thereof a compound of Formula I:

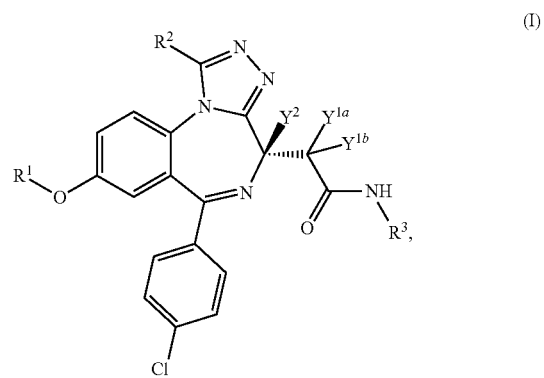

or a pharmaceutically acceptable salt thereof, wherein
$Y^{1a}$ and $Y^{1b}$ are the same and are hydrogen or deuterium;
$Y^2$ is hydrogen or deuterium;
$R^1$ and $R^2$ are each independently selected from $CH_3$ and $CD_3$;
$R^3$ is selected from $CH_2CH_3$, $CH_2CD_3$, $CD_2CH_3$, and $CD_2CD_3$; and
if $R^1$ and $R^2$ are each $CH_3$, $R^3$ is $CH_2CH_3$, and $Y^2$ is hydrogen, then $Y^{1a}$ and $Y^{1b}$ are each deuterium; and wherein any atom not designated as deuterium is present at its natural isotopic abundance.

2. The method of claim 1, wherein the inflammatory condition is dermatitis.

3. The method of claim 1, wherein the inflammatory bowel disease is Crohn's disease or ulcerative colitis.

4. The method of claim 1, wherein for the compound of Formula I, $Y^{1a}$ and $Y^{1b}$ are hydrogen.

5. The method of claim 1, wherein for the compound of Formula I, $Y^{1a}$ and $Y^{1b}$ are deuterium.

6. The method of claim 1, wherein for the compound of Formula I, $R^3$ is selected from $CH_2CH_3$ and $CD_2CD_3$.

7. The method of claim 4, wherein the compound of Formula I is selected from any one of the compounds set forth in the table below:

| Compound | $Y^2$ | $R^1$ | $R^2$ | $R^3$ |
|---|---|---|---|---|
| 101 | H | —$CH_3$ | —$CH_3$ | —$CD_2CD_3$ |
| 102 | H | —$CH_3$ | —$CH_3$ | —$CD_2CH_3$ |
| 103 | H | —$CH_3$ | —$CH_3$ | —$CH_2CD_3$ |
| 104 | H | —$CD_3$ | —$CH_3$ | —$CH_2CH_3$ |
| 105 | H | —$CH_3$ | —$CD_3$ | —$CH_2CH_3$ |
| 106 | D | —$CH_3$ | —$CH_3$ | —$CH_2CH_3$ |
| 107 | D | —$CD_3$ | —$CH_3$ | —$CH_2CH_3$ |
| 108 | D | —$CH_3$ | —$CD_3$ | —$CH_2CH_3$ |
| 109 | D | —$CH_3$ | —$CH_3$ | —$CD_2CD_3$ |
| 110 | D | —$CH_3$ | —$CH_3$ | —$CD_2CH_3$ |
| 111 | D | —$CH_3$ | —$CH_3$ | —$CH_2CD_3$ |
| 112 | H | —$CD_3$ | —$CD_3$ | —$CH_2CH_3$ |
| 113 | H | —$CD_3$ | —$CH_3$ | —$CD_2CD_3$ |
| 114 | H | —$CD_3$ | —$CH_3$ | —$CD_2CH_3$ |
| 115 | H | —$CD_3$ | —$CH_3$ | —$CH_2CD_3$ |
| 116 | H | —$CH_3$ | —$CD_3$ | —$CD_2CD_3$ |
| 117 | H | —$CH_3$ | —$CD_3$ | —$CD_2CH_3$ |
| 118 | H | —$CH_3$ | —$CD_3$ | —$CH_2CD_3$ |
| 119 | D | —$CD_3$ | —$CD_3$ | —$CH_2CH_3$ |
| 120 | D | —$CD_3$ | —$CH_3$ | —$CD_2CD_3$ |
| 121 | D | —$CD_3$ | —$CH_3$ | —$CD_2CH_3$ |
| 122 | D | —$CD_3$ | —$CH_3$ | —$CH_2CD_3$ |

-continued

| Compound | $Y^2$ | $R^1$ | $R^2$ | $R^3$ |
|---|---|---|---|---|
| 123 | D | —CH$_3$ | —CD$_3$ | —CD$_2$CD$_3$ |
| 124 | D | —CH$_3$ | —CD$_3$ | —CD$_2$CH$_3$ |
| 125 | D | —CH$_3$ | —CD$_3$ | —CH$_2$CD$_3$ |
| 126 | H | —CD$_3$ | —CD$_3$ | —CD$_2$CD$_3$ |
| 127 | H | —CD$_3$ | —CD$_3$ | —CD$_2$CH$_3$ |
| 128 | H | —CD$_3$ | —CD$_3$ | —CH$_2$CD$_3$ |
| 129 | D | —CD$_3$ | —CD$_3$ | —CD$_2$CD$_3$ |
| 130 | D | —CD$_3$ | —CD$_3$ | —CD$_2$CH$_3$ |
| 131 | D | —CD$_3$ | —CD$_3$ | —CH$_2$CD$_3$ | or a pharmaceutically acceptable salt thereof.

8. The method of claim 5, wherein the compound of Formula I is selected from any one of the compounds set forth in the table below:

| Compound | $Y^2$ | $R^1$ | $R^2$ | $R^3$ |
|---|---|---|---|---|
| 200 | H | —CH$_3$ | —CH$_3$ | —CH$_2$CH$_3$ |
| 201 | H | —CH$_3$ | —CH$_3$ | —CD$_2$CD$_3$ |
| 202 | H | —CH$_3$ | —CH$_3$ | —CD$_2$CH$_3$ |
| 203 | H | —CH$_3$ | —CH$_3$ | —CH$_2$CD$_3$ |
| 204 | H | —CD$_3$ | —CH$_3$ | —CH$_2$CH$_3$ |
| 205 | H | —CH$_3$ | —CD$_3$ | —CH$_2$CH$_3$ |
| 206 | D | —CH$_3$ | —CH$_3$ | —CH$_2$CH$_3$ |
| 207 | D | —CD$_3$ | —CH$_3$ | —CH$_2$CH$_3$ |
| 208 | D | —CH$_3$ | —CD$_3$ | —CH$_2$CH$_3$ |
| 209 | D | —CH$_3$ | —CH$_3$ | —CD$_2$CD$_3$ |
| 210 | D | —CH$_3$ | —CH$_3$ | —CD$_2$CH$_3$ |
| 211 | D | —CH$_3$ | —CH$_3$ | —CH$_2$CD$_3$ |
| 212 | H | —CD$_3$ | —CD$_3$ | —CH$_2$CH$_3$ |
| 213 | H | —CD$_3$ | —CH$_3$ | —CD$_2$CD$_3$ |
| 214 | H | —CD$_3$ | —CH$_3$ | —CD$_2$CH$_3$ |
| 215 | H | —CD$_3$ | —CH$_3$ | —CH$_2$CD$_3$ |
| 216 | H | —CH$_3$ | —CD$_3$ | —CD$_2$CD$_3$ |
| 217 | H | —CH$_3$ | —CD$_3$ | —CD$_2$CH$_3$ |
| 218 | H | —CH$_3$ | —CD$_3$ | —CH$_2$CD$_3$ |
| 219 | D | —CD$_3$ | —CD$_3$ | —CH$_2$CH$_3$ |
| 220 | D | —CD$_3$ | —CH$_3$ | —CD$_2$CD$_3$ |
| 221 | D | —CD$_3$ | —CH$_3$ | —CD$_2$CH$_3$ |
| 222 | D | —CD$_3$ | —CH$_3$ | —CH$_2$CD$_3$ |
| 223 | D | —CH$_3$ | —CD$_3$ | —CD$_2$CD$_3$ |
| 224 | D | —CH$_3$ | —CD$_3$ | —CD$_2$CH$_3$ |
| 225 | D | —CH$_3$ | —CD$_3$ | —CH$_2$CD$_3$ |
| 226 | H | —CD$_3$ | —CD$_3$ | —CD$_2$CD$_3$ |
| 227 | H | —CD$_3$ | —CD$_3$ | —CD$_2$CH$_3$ |
| 228 | H | —CD$_3$ | —CD$_3$ | —CH$_2$CD$_3$ |
| 229 | D | —CD$_3$ | —CD$_3$ | —CD$_2$CD$_3$ |
| 230 | D | —CD$_3$ | —CD$_3$ | —CD$_2$CH$_3$ |
| 231 | D | —CD$_3$ | —CD$_3$ | —CH$_2$CD$_3$ | or a pharmaceutically acceptable salt thereof.

9. The method of claim 1, wherein for the compound of Formula I, the compound has an isotopic enrichment factor for each designated deuterium atom of at least 6000 (90% deuterium incorporation).

10. The method of claim 1, wherein for the compound of Formula I, the compound has an isotopic enrichment factor for each designated deuterium atom of at least 6333.3 (95% deuterium incorporation).

11. The method of claim 7, wherein the compound of Formula I is selected from any one of the compounds set forth in the table below:

| Compound | $Y^2$ | $R^1$ | $R^2$ | $R^3$ |
|---|---|---|---|---|
| 101 | H | —CH$_3$ | —CH$_3$ | —CD$_2$CD$_3$ |
| 105 | H | —CH$_3$ | —CD$_3$ | —CH$_2$CH$_3$ |
| 108 | D | —CH$_3$ | —CD$_3$ | —CH$_2$CH$_3$ |
| 109 | D | —CH$_3$ | —CH$_3$ | —CD$_2$CD$_3$ |
| 112 | H | —CD$_3$ | —CD$_3$ | —CH$_2$CH$_3$ |
| 113 | H | —CD$_3$ | —CH$_3$ | —CD$_2$CD$_3$ |
| 116 | H | —CH$_3$ | —CD$_3$ | —CD$_2$CD$_3$ |
| 117 | H | —CH$_3$ | —CD$_3$ | —CD$_2$CH$_3$ |
| 118 | H | —CH$_3$ | —CD$_3$ | —CH$_2$CD$_3$ |
| 119 | D | —CD$_3$ | —CD$_3$ | —CH$_2$CH$_3$ |
| 120 | D | —CD$_3$ | —CH$_3$ | —CD$_2$CD$_3$ |
| 123 | D | —CH$_3$ | —CD$_3$ | —CD$_2$CD$_3$ |
| 124 | D | —CH$_3$ | —CD$_3$ | —CD$_2$CH$_3$ |
| 125 | D | —CH$_3$ | —CD$_3$ | —CH$_2$CD$_3$ |
| 126 | H | —CD$_3$ | —CD$_3$ | —CD$_2$CD$_3$ |
| 127 | H | —CD$_3$ | —CD$_3$ | —CD$_2$CH$_3$ |
| 128 | H | —CD$_3$ | —CD$_3$ | —CH$_2$CD$_3$ |
| 129 | D | —CD$_3$ | —CD$_3$ | —CD$_2$CD$_3$ |
| 130 | D | —CD$_3$ | —CD$_3$ | —CD$_2$CH$_3$ |
| 131 | D | —CD$_3$ | —CD$_3$ | —CH$_2$CD$_3$ | or a pharmaceutically acceptable salt thereof, wherein the compound has an isotopic enrichment factor for each designated deuterium atom of at least 6000 (90% deuterium incorporation).

12. The method of claim 8, wherein the compound of Formula I is selected from any one of the compounds set forth in the table below:

| Compound | $Y^2$ | $R^1$ | $R^2$ | $R^3$ |
|---|---|---|---|---|
| 201 | H | —CH$_3$ | —CH$_3$ | —CD$_2$CD$_3$ |
| 205 | H | —CH$_3$ | —CD$_3$ | —CH$_2$CH$_3$ |
| 208 | D | —CH$_3$ | —CD$_3$ | —CH$_2$CH$_3$ |
| 209 | D | —CH$_3$ | —CH$_3$ | —CD$_2$CD$_3$ |
| 212 | H | —CD$_3$ | —CD$_3$ | —CH$_2$CH$_3$ |
| 213 | H | —CD$_3$ | —CH$_3$ | —CD$_2$CD$_3$ |
| 216 | H | —CH$_3$ | —CD$_3$ | —CD$_2$CD$_3$ |
| 217 | H | —CH$_3$ | —CD$_3$ | —CD$_2$CH$_3$ |
| 218 | H | —CH$_3$ | —CD$_3$ | —CH$_2$CD$_3$ |
| 219 | D | —CD$_3$ | —CD$_3$ | —CH$_2$CH$_3$ |
| 220 | D | —CD$_3$ | —CH$_3$ | —CD$_2$CD$_3$ |
| 223 | D | —CH$_3$ | —CD$_3$ | —CD$_2$CD$_3$ |
| 224 | D | —CH$_3$ | —CD$_3$ | —CD$_2$CH$_3$ |
| 225 | D | —CH$_3$ | —CD$_3$ | —CH$_2$CD$_3$ |
| 226 | H | —CD$_3$ | —CD$_3$ | —CD$_2$CD$_3$ |
| 227 | H | —CD$_3$ | —CD$_3$ | —CD$_2$CH$_3$ |
| 228 | H | —CD$_3$ | —CD$_3$ | —CH$_2$CD$_3$ |
| 229 | D | —CD$_3$ | —CD$_3$ | —CD$_2$CD$_3$ |
| 230 | D | —CD$_3$ | —CD$_3$ | —CD$_2$CH$_3$ |
| 231 | D | —CD$_3$ | —CD$_3$ | —CH$_2$CD$_3$ | or a pharmaceutically acceptable salt thereof, wherein the compound has an isotopic enrichment factor for each designated deuterium atom of at least 6000 (90% deuterium incorporation).

13. The method of claim 11, wherein for the compound of Formula I, the compound has an isotopic enrichment factor for each designated deuterium atom of at least 6333.3 (95% deuterium incorporation).

14. The method of claim 12, wherein for the compound of Formula I, the compound has an isotopic enrichment factor for each designated deuterium atom of at least 6333.3 (95% deuterium incorporation).

* * * * *